United States Patent
Chivukula et al.

(10) Patent No.: US 10,519,447 B2
(45) Date of Patent: Dec. 31, 2019

(54) THERAPEUTIC UNA OLIGOMERS AND USES THEREOF

(71) Applicant: Arcturus Therapeutics, Inc., San Diego, CA (US)

(72) Inventors: Padmanabh Chivukula, San Diego, CA (US); Kiyoshi Tachikawa, San Diego, CA (US); Joseph E. Payne, San Diego, CA (US)

(73) Assignee: ARCTURUS THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 15/563,579

(22) PCT Filed: Apr. 1, 2016

(86) PCT No.: PCT/US2016/025578
§ 371 (c)(1),
(2) Date: Sep. 30, 2017

(87) PCT Pub. No.: WO2016/161299
PCT Pub. Date: Oct. 6, 2016

(65) Prior Publication Data
US 2018/0105816 A1 Apr. 19, 2018

Related U.S. Application Data

(60) Provisional application No. 62/141,261, filed on Apr. 1, 2015.

(51) Int. Cl.
| | |
|---|---|
| *C12N 15/113* | (2010.01) |
| *A61P 9/00* | (2006.01) |
| *A61P 31/14* | (2006.01) |
| *A61P 25/00* | (2006.01) |

(52) U.S. Cl.
CPC ............ *C12N 15/1131* (2013.01); *A61P 9/00* (2018.01); *A61P 25/00* (2018.01); *A61P 31/14* (2018.01); *C12N 15/113* (2013.01); *C12N 15/1137* (2013.01); *C12N 2310/14* (2013.01); *C12N 2310/315* (2013.01); *C12N 2310/321* (2013.01); *C12N 2310/322* (2013.01); *C12N 2310/323* (2013.01); *C12N 2310/346* (2013.01); *C12N 2320/51* (2013.01); *C12N 2320/52* (2013.01)

(58) Field of Classification Search
None
See application file for complete search history.

(56) References Cited

U.S. PATENT DOCUMENTS

| | | |
|---|---|---|
| 4,199,574 A | 4/1980 | Schaeffer |
| 4,968,686 A | 11/1990 | Townsend |
| 5,786,359 A | 7/1998 | Reitz |
| 5,898,031 A | 4/1999 | Crooke |
| 6,037,176 A | 3/2000 | Bennett |
| 6,069,132 A | 5/2000 | Revanker |
| 6,506,559 B1 | 1/2003 | Fire et al. |
| 6,608,035 B1 | 8/2003 | Agrawal |
| 6,753,139 B1 | 6/2004 | Baulcombe |
| 7,056,704 B2 | 6/2006 | Tuschl |
| 7,078,196 B2 | 7/2006 | Tuschl |
| 7,459,547 B2 | 12/2008 | Zamore et al. |
| 7,579,451 B2 | 8/2009 | Manoharan |
| 7,691,995 B2 | 4/2010 | Zamore |
| 7,745,608 B2 | 6/2010 | Manoharan |
| 7,750,144 B2 | 7/2010 | Zamore |
| 7,786,290 B2 | 8/2010 | Woppmann |
| 7,915,399 B2 | 3/2011 | MacLachlan |
| 8,101,584 B2 | 1/2012 | Kreutzer |
| 8,101,742 B2 | 1/2012 | Kreutzer |
| 8,258,285 B2 | 9/2012 | Baulcombe |
| 8,362,231 B2 | 1/2013 | Tuschl |
| 8,420,391 B2 | 4/2013 | Tuschl |
| 8,546,143 B2 | 10/2013 | Kreutzer |
| 9,365,610 B2 | 6/2016 | Payne |
| 9,856,475 B2 * | 1/2018 | Tachikawa ............. A61K 9/127 |
| 9,982,259 B2 * | 5/2018 | Tachikawa ............. A61K 9/127 |
| 2002/0086356 A1 | 7/2002 | Tuschl |
| 2003/0143732 A1 | 7/2003 | Fosnaugh |
| 2004/0171570 A1 | 9/2004 | Allerson |
| 2004/0175703 A1 | 9/2004 | Kreutzer et al. |
| 2004/0192626 A1 | 9/2004 | McSwiggen et al. |

(Continued)

FOREIGN PATENT DOCUMENTS

| | | |
|---|---|---|
| WO | WO-9629336 A1 | 9/1996 |
| WO | WO-96029336 A1 | 9/1996 |

(Continued)

OTHER PUBLICATIONS

Bartlett, "Effect of siRNA Nuclease Stability on the In Vitro and In Vivo Kinetics of siRNA-Mediated Gene Silencing," Biotechnology and Bioengineering, vol. 97, No. 4, Jul. 1, 2007.

Bramsen et al., "A large-scale chemical modification screen identifies design rules to generate siRNAs with high activity, high stability and low toxicity," Nucleic Acids Research 2009, vol. 37, No. 9, pp. 2867-2881.

Bramsen, Jesper B., et al., "A screen of chemical modifications identifies position-specific modification by UNA to most potently reduce siRNA off-target effects." Nucleic acids research 38.17 (2010): 5761-5773.

Czauderna, Frank, et al., "Structural variations and stabilising modifications of synthetic siRNAs in mammalian cells." Nucleic acids research 31.11 (2003): 2705-2716.

(Continued)

*Primary Examiner* — J. E. Angell
(74) *Attorney, Agent, or Firm* — Mintz, Levin, Cohn, Ferris, Glovsky and Popeo, P.C.

(57) ABSTRACT

This invention provides UNA oligomers for regulating the expression of a target gene. The UNA oligomers contain UNA monomer linkers, and may contain one or more nucleotides modified with a 2'-O-methyl group, one or more nucleotides modified with a 2'-deoxy-2'-fluoro group, and one or more phosphorothioate or chiral phosphorothioate intermonomer linkages. UNA oligomers can be used as active agents for preventing or treating disease.

9 Claims, No Drawings

Specification includes a Sequence Listing.

(56) References Cited

U.S. PATENT DOCUMENTS

| | | |
|---|---|---|
| 2004/0259247 A1 | 12/2004 | Tuschl et al. |
| 2004/0261149 A1 | 12/2004 | Fauquet et al. |
| 2005/0100907 A1 | 5/2005 | Kreutzer |
| 2005/0107325 A1 | 5/2005 | Manoharan |
| 2005/0129778 A1 | 6/2005 | Mulye |
| 2005/0223427 A1 | 10/2005 | Khvorova |
| 2005/0244858 A1 | 11/2005 | Rossi et al. |
| 2005/0288244 A1 | 12/2005 | Manoharan |
| 2006/0122391 A1 | 6/2006 | Babu |
| 2006/0276635 A1 | 12/2006 | McSwiggen |
| 2006/0287260 A1 | 12/2006 | Manoharan |
| 2007/0275914 A1 | 11/2007 | Manoharan |
| 2009/0093438 A1 | 4/2009 | McSwiggen |
| 2010/0120893 A1 | 5/2010 | Baligh et al. |
| 2011/0136233 A1 | 6/2011 | Quay et al. |
| 2011/0313020 A1 | 12/2011 | Templin et al. |
| 2012/0120893 A1 | 5/2012 | Baligh et al. |
| 2012/0225927 A1 | 9/2012 | Sah |
| 2013/0096289 A1 | 4/2013 | Wengel |
| 2013/0190383 A1 | 7/2013 | Vaish et al. |
| 2014/0315835 A1 | 10/2014 | Rajeev |
| 2015/0141678 A1 | 5/2015 | Payne |
| 2015/0307880 A1 | 10/2015 | Tachikawa |
| 2015/0307881 A1 | 10/2015 | Tachikawa et al. |

FOREIGN PATENT DOCUMENTS

| | | | |
|---|---|---|---|
| WO | WO-9908688 A1 | 2/1999 | |
| WO | WO-99008688 A1 | 2/1999 | |
| WO | WO-2003004602 A2 | 1/2003 | |
| WO | WO-2003037909 A1 | 5/2003 | |
| WO | WO-03070918 A2 | 8/2003 | |
| WO | WO-03106477 A1 | 12/2003 | |
| WO | WO-2004090105 A2 | 10/2004 | |
| WO | WO-2004090108 A2 | 10/2004 | |
| WO | WO-2004094595 A2 | 11/2004 | |
| WO | WO-2004108897 A2 | 12/2004 | |
| WO | WO-2005089268 A2 | 9/2005 | |
| WO | WO-2005089287 A2 | 9/2005 | |
| WO | WO-2005121372 A2 | 12/2005 | |
| WO | WO-06085987 A2 | 8/2006 | |
| WO | WO-2006112872 A2 | 10/2006 | |
| WO | WO-2007022369 A2 | 2/2007 | |
| WO | WO-2007051303 A1 | 5/2007 | |
| WO | WO-2007056829 A1 | 5/2007 | |
| WO | WO-2008020435 A2 | 2/2008 | |
| WO | WO-08147824 A2 | 12/2008 | |
| WO | WO-2011123468 A1 | 10/2011 | |
| WO | WO-2011133584 A2 | 10/2011 | |
| WO | WO-2014037436 A1 | 3/2014 | |
| WO | WO-2015042564 A1 * | 3/2015 | ........... C12N 15/113 |

OTHER PUBLICATIONS

Elbashir, Sayda M., et al. "Functional anatomy of siRNAs for mediating efficient RNAi in *Drosophila melanogaster* embryo lysate." The EMBO journal 20.23 (2001): 6877-6888.

Habus, "Oligonucleotides Containing Acyclic Nucleoside Analogues with Carbamate Internucleoside Linkages," Nucleosides & Nucleotides, 1995, vol. 14 (9&10), 1853-1859.

Jensen, T. et al., "Unlocked Nucleic Acid (UNA) and UNA Derivatives: Thermal Denaturation Studies;" Nucleic Acids Symposium Series No. 52; Oxford University Press 2008; pp. 133-134.

John Wiley & Sons, Inc.; "IUPAC-IUB Joint Commission on Biochemical Nomenclature Abbreviations and Symbols for the Description of Conformations of Polynucleotide Chains;" Current Protocols in Nucleic Acid Chemistry 2000; pp. A.1C.1-A.1D.3.

Langkjær, Niels, et al., "UNA (unlocked nucleic acid): a flexible RNA mimic that allows engineering of nucleic acid duplex stability." Bioorganic & medicinal chemistry 17.15 (2009): 5420-5425.

Laursen, Maria B., et al., "Utilization of unlocked nucleic acid (UNA) to enhance siRNA performance in vitro and in vivo." Molecular BioSystems 6.5 (2010): 862-870.

Layzer, "In vivo activity of nuclease-resistant siRNAs," RNA (2004), vol. 10, pp. 766-771.

Mangos, M. et al., "Efficient RNase H-Directed Cleavage of RNA Promoted by Antisense DNA or 2'F-ANA Constructs Containing Acyclic Nucleotide Inserts;" Journal of the American Chemical Society 2003; vol. 125; pp. 654-661.

Nielsen, "Oligonucleotide Analogues Containing 4'-C-(Hydroxymethyl)uridine: Synthesis, Evaluation and Mass Spectrometric Analysis," Bioorganic & Medicinal Chemistry, vol. 3, No. 11, pp. 1493-1502, 1995.

Nielsen, P. et al.; "Synthesis and Evaluation of Oligodeoxynucleotides Containing Acyclic Nucleosides: Introduction of Three Novel Analogues and a Summary;" Bioorganic & Medicinal Chemistry; Elsevier Science Ltd 1995; vol. 3; No. 1; pp. 19-28.

Pandolfi, "Evaluation of Different Types of End-Capping Modifications on the Stability of Oligonucleotides Toward 3'- and 5' Exonucleases," Nucleosides & Nucleotides, 1999, vol. 18 (9), 2051-2069.

Pei et al., "Synthesis of 3'-C-Hydroxymethyl-substituted Pyrimidine and Purine Nucleosides as Potential Anti-Hepatitis C Virus (HCV) Agents," Arch Pharm Res 2009, vol. 31, No. 7, pp. 843-849.

Petersen, "LNA: A versatile tool for therapeutics and genomics," Trends in Biotechnology vol. 21 No. 2 Feb. 2003.

Pfundheller, "Locked Nucleic Acid Synthesis," Chapter 8 in Methods in Molecular Biology, vol. 288: Oligonucleotide Synthesis: Methods and Applications, Edited by: P. Herdewijn, Humana Press, 2005.

pharmabiz.com, Arcturus to present gene knockdown data in non-human primates, showing up to 94% reduction in gene expression with single low dose, dated Oct. 14, 2014.

Snead, Nicholas M., et al., "5' Unlocked nucleic acid modification improves siRNA targeting." Molecular Therapy-Nucleic Acids 2 (2013): 7 Pages.

Thrane, H. et al.; "Novel Linear and Branched Oligodeoxynucleotide Analogues Containing 4'-C-(Hydroxymethyl Thymidine;" Tetrahedron; Elsevier Science Ltd 1995; vol. 51; No. 37; pp. 10389-10402.

Vaish, Narendra, et al., "Improved specificity of gene silencing by siRNAs containing unlocked nucleobase analogs." Nucleic acids research 39.5 (2010): 1823-1832.

Werk, Denise, et al., "Application of small interfering RNAs modified by unlocked nucleic acid (UNA) to inhibit the heart-pathogenic coxsackievirus B3." FEBS letters 584.3 (2010): 591-598.

Supplementary Search Report for counterpart application No. EP16774322.8 dated Feb. 11, 2018.

* cited by examiner

THERAPEUTIC UNA OLIGOMERS AND USES THEREOF

TECHNICAL FIELD OF THE INVENTION

This invention relates to the fields of biopharmaceuticals and therapeutics composed of oligomers for gene silencing. More particularly, this invention relates to methods, structures and compositions for oligomers that are stable, long acting agents for gene regulation.

SEQUENCE LISTING

This application includes a Sequence Listing submitted electronically as an ASCII file, named ARC1321WO_SL.txt, and is hereby incorporated by reference in its entirety.

BACKGROUND OF THE INVENTION

A problem for RNA interference methodologies has been to provide structures having long lifetimes in vivo for longer acting therapeutic agents. One challenge is to develop delivery agents that maintain the active agent in the circulation for longer periods, or in other biological environments.

Conventional approaches to the problem include incorporating modifications into the nucleotides of a siRNA or other nucleic acid agent to enhance its longevity. However, these methods must avoid a significant trade-off of activity for stability.

Another drawback of conventional methods is the limited availability of structural modifications that can be incorporated into nucleotides.

Moreover, nucleotides with structural modifications have so far provided only marginal improvement in the properties of gene silencing and RNA agents.

What is needed are structures and compositions that provide stable, long acting pharmaceutical ingredients for gene silencing and therapeutic strategies.

There is a continuing need for molecules that are active in RNA interference, as well as other modalities, with structures that provide long lifetimes in vivo for longer acting galenic agents.

BRIEF SUMMARY

This invention provides oligomer structures for therapeutic agents that are long acting in their effect on gene regulation and modulation when used in vitro or administered in vivo.

The oligomeric structures of this invention can contain one or more UNA monomers.

This invention provides structures, methods and compositions for UNA-containing oligomeric agents that incorporate UNA monomers. The UNA oligomeric molecules of this invention can be used as active agents in formulations for gene silencing therapeutics.

Among other things, this invention provides unique oligomer structures that incorporate novel combinations of UNA monomers with certain natural nucleotides, non-natural nucleotides, modified nucleotides, or chemically-modified nucleotides.

Aspects of this disclosure include UNA Oligomers that are pharmacologically active molecules. The UNA Oligomers of this invention can be used as single-stranded or double-stranded active pharmaceutical ingredients for regulating or modulating gene expression, and in RNA interference methods, as well as antisense strategies.

Embodiments of this disclosure provide a wide range of novel UNA oligomer molecules, which incorporate one or more UNA monomers.

In some aspects, this invention provides long acting UNA oligomers having structures that incorporate novel combinations of UNA monomers with certain natural nucleotides, non-natural nucleotides, modified nucleotides, or chemically-modified nucleotides.

In further aspects, this invention provides therapeutics for preventing, ameliorating, or treating a disease.

In additional aspects, a compound of this invention may be used in the manufacture of a medicament for, or in the prevention or treatment of a viral infection including hepatitis, amyloidosis and related diseases, a cancer, a metabolic disease, an inflammatory disease, a liver disease, a heart disease, a skin disease, or a bone disease.

Embodiments of this invention include the following:

A UNA oligomer having a first strand and a second strand, each of the strands being 19-29 monomers in length, the monomers comprising UNA monomers and nucleic acid monomers, wherein the oligomer has a duplex structure of from 14 to 29 monomers in length, wherein the second strand is a guide strand for RNA interference and the first strand is a passenger strand for RNA interference, and wherein the UNA oligomer reduces expression of a target gene.

A UNA oligomer can have one or more chemical modifications of one or more of the nucleic acid monomers in each strand. In some embodiments, a oligomer can contain one or more nucleotides modified with a 2'-O-methyl group, or from one to nine nucleotides modified with a 2'-O-methyl group, or one or more nucleotides modified with a 2'-deoxy-2'-fluoro group, or one or more of the intermonomer linkages in either strand being a phosphorothioate or chiral phosphorothioate linkage.

A UNA oligomer can be targeted to any human, bacterial or viral target gene, including a viral gene of Hepatitis B virus, TTR, APOB, PCSK9, and APOC3, among others.

In some embodiments, a UNA oligomer can have long lasting activity in vitro.

In certain embodiments, a UNA oligomer can have long lasting potency in vivo.

Embodiments of this invention include pharmaceutical compositions having one or more UNA oligomers and a pharmaceutically acceptable carrier, diluent, or adjuvant.

Uses of a UNA oligomer include to regulate expression of a target gene.

In some aspects, a use of a UNA oligomer can include preventing or treating Hepatitis B infection, amyloid neuropathy, amyloidosis, amyloidosis related to transthyretin, hypercholesterolemia, cholesterol disorder, hypertriglyceridemia, or lipoprotein disorder in a subject in need thereof.

In certain embodiments, a use of a UNA oligomer can include the preparation of a medicament for a therapeutic target.

In certain aspects, a use of a UNA oligomer can include the preparation of a medicament for decreasing expression level of a target mRNA in a cell.

DETAILED DESCRIPTION OF THE INVENTION

This invention provides oligomer structures for therapeutic agents that are long acting in their effect on gene regulation when used in vitro or administered in vivo. The oligomeric structures of this invention contain one or more UNA monomers.

This invention provides structures, methods and compositions for UNA monomer-containing oligomeric agents that incorporate UNA monomers. The UNA oligomeric molecules of this invention can be used as active agents in formulations for gene silencing therapeutics.

Among other things, this invention provides unique oligomer structures that incorporate novel combinations of UNA monomers with certain natural nucleotides, non-natural nucleotides, modified nucleotides, or chemically-modified nucleotides.

Aspects of this disclosure include UNA monomer-containing oligomers that are pharmacologically active molecules. The UNA Oligomers of this invention can be used as active pharmaceutical ingredients for regulating or modulating gene expression, RNA interference methods, as well as antisense strategies.

Embodiments of this disclosure provide a wide range of novel UNA oligomer molecules, which incorporate one or more UNA monomer linkers.

In some aspects, this invention provides long acting UNA Oligomers having structures that incorporate novel combinations of UNA Monomers with certain natural nucleotides, non-natural nucleotides, modified nucleotides, or chemically-modified nucleotides.

In some aspects, this invention provides long acting properties for gene silencing drugs, and can reduce the dose levels required for efficacious therapy.

In certain aspects, this invention can provide UNA oligomers having increased activity in vitro.

In some embodiments, this invention can provide UNA oligomers having increased potency in vivo.

In additional embodiments, this invention can provide UNA oligomers having longer functional half-life.

In certain embodiments, this invention can provide UNA oligomers having long lasting activity in vitro.

In particular embodiments, this invention can provide UNA oligomers having long lasting potency in vivo.

Embodiments of this invention may further provide UNA oligomers having increased enzymatic stability.

UNA oligomers of this disclosure can provide enhanced stability, in vitro and in vivo, for modulating gene expression.

In further aspects of this invention, UNA oligomers can exhibit reduced side effects as agents for treatment of a disease or condition. In some embodiments, a UNA oligomer can exhibit reduced off target effects as an agent for treating a disease, or in vitro.

UNA Monomers

UNA monomers are small organic molecules based on a propane-1,2,3-tri-yl-trisoxy structure as shown below:

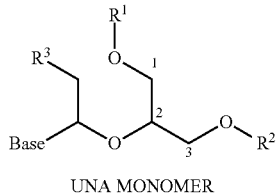

UNA MONOMER where $R^1$ and $R^2$ are H, and $R^1$ and $R^2$ can be phosphodiester linkages, Base can be a nucleobase, and $R^3$ is a functional group described below.

In another view, the UNA monomer main atoms can be drawn in IUPAC notation as follows:

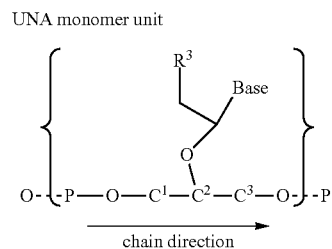

where the direction of progress of the oligomer chain is from the 1-end to the 3-end of the propane residue.

Examples of a nucleobase include uracil, thymine, cytosine, 5-methylcytosine, adenine, guanine, inosine, and natural and non-natural nucleobase analogues.

In general, because the UNA monomers are not nucleotides, they can exhibit at least four forms in an oligomer. First, a UNA monomer can be an internal monomer in an oligomer, where the UNA monomer is flanked by other monomers on both sides. In this form, the UNA monomer can participate in base pairing when the oligomer is a duplex, for example, and there are other monomers with nucleobases in the duplex.

Examples of UNA monomer as internal monomers flanked at both the propane-1-yl position and the propane-3-yl position, where $R^3$ is —OH, are shown below.

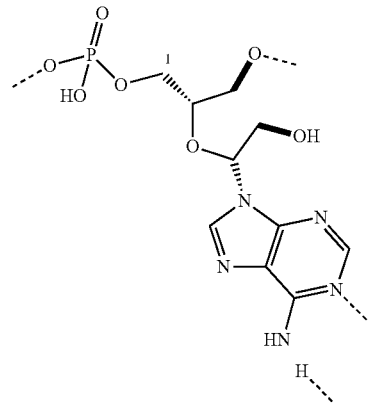

UNA-A

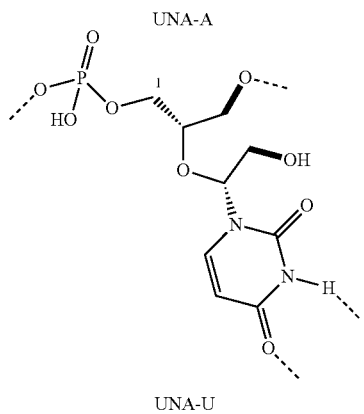

UNA-U

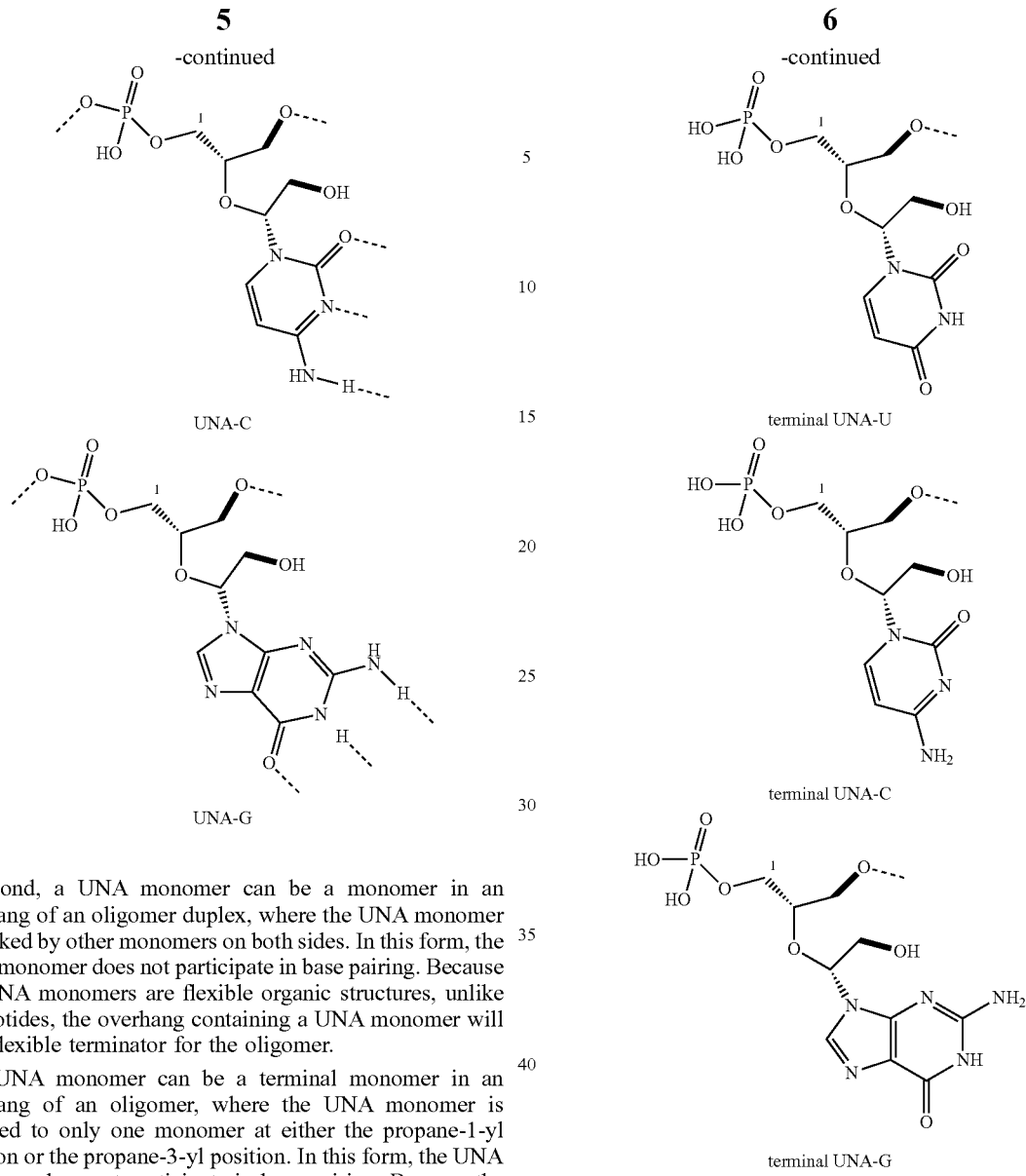

UNA-C

UNA-G

Second, a UNA monomer can be a monomer in an overhang of an oligomer duplex, where the UNA monomer is flanked by other monomers on both sides. In this form, the UNA monomer does not participate in base pairing. Because the UNA monomers are flexible organic structures, unlike nucleotides, the overhang containing a UNA monomer will be a flexible terminator for the oligomer.

A UNA monomer can be a terminal monomer in an overhang of an oligomer, where the UNA monomer is attached to only one monomer at either the propane-1-yl position or the propane-3-yl position. In this form, the UNA monomer does not participate in base pairing. Because the UNA monomers are flexible organic structures, unlike nucleotides, the overhang containing a UNA monomer can be a flexible terminator for the oligomer.

Examples of a UNA monomer as a terminal monomer attached at the propane-3-yl position are shown below.

terminal UNA-A terminal UNA-U terminal UNA-C terminal UNA-G

Because a UNA monomer can be a flexible molecule, a UNA monomer as a terminal monomer can assume widely differing conformations. An example of an energy minimized UNA monomer conformation as a terminal monomer attached at the propane-3-yl position is shown below.

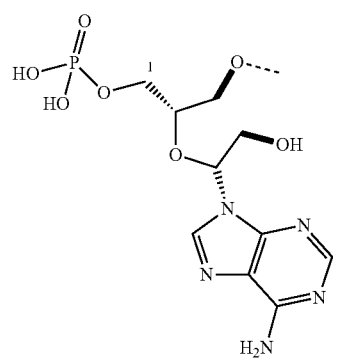

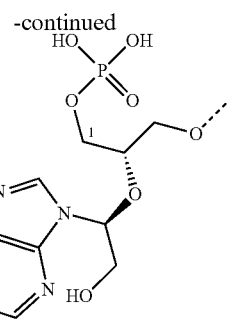

UNA-A terminal forms: the dashed bond shows
the propane-3-yl attachment

Thus, UNA oligomers having a terminal UNA monomer are significantly different in structure from conventional nucleic acid agents, such as siRNAs. For example, siRNAs may require that terminal monomers or overhangs in a duplex be stabilized. In contrast, the conformability of a terminal UNA monomer can provide UNA oligomers with different properties.

Among other things, the structure of the UNA monomer allows it to be attached to naturally-occurring nucleotides. A UNA oligomer can be a chain composed of UNA monomers, as well as various nucleotides that may be based on naturally-occurring nucleosides.

In some embodiments, the functional group $R^3$ of a UNA monomer can be —$OR^4$, —$SR^4$, —$NR^4{}_2$, —$NH(C=O)R^4$, morpholino, morpholin-1-yl, piperazin-1-yl, or 4-alkanoyl-piperazin-1-yl, where $R^4$ is the same or different for each occurrence, and can be H, alkyl, a cholesterol, a lipid molecule, a polyamine, an amino acid, or a polypeptide.

The UNA monomers are organic molecules. UNA monomers are not nucleic acid monomers or nucleotides, nor are they naturally-occurring nucleosides or modified naturally-occurring nucleosides.

A UNA oligomer of this invention is a synthetic chain molecule. A UNA oligomer of this invention is not a nucleic acid, nor an oligonucleotide.

In some embodiments, as shown above, a UNA monomer can be UNA-A (designated Ã), UNA-U (designated Ũ), UNA-C (designated C̆), and UNA-G (designated Ğ).

Designations that may be used herein include mA, mG, mC, and mU, which refer to the 2'-O-methyl modified ribonucleotides.

Designations that may be used herein include lower case c and u, which refer to the 2'-O-methyl modified ribonucleotides.

Designations that may be used herein include dT, which refers to a 2'-deoxy T nucleotide.

Designations that may be used herein include *, which refers to a phosphorothioate linkage.

Monomers for UNA Oligomers

As used herein, in the context of oligomer sequences, the symbol X represents a UNA monomer.

As used herein, in the context of oligomer sequences, the symbol N represents any natural nucleotide monomer, or a modified nucleotide monomer.

As used herein, in the context of oligomer sequences, the symbol Q represents a non-natural, modified, or chemically-modified nucleotide monomer.

When a Q monomer appears in one strand of the oligomer, and is unpaired with the other strand, the monomer can have any base attached. When a Q monomer appears in one strand of the oligomer, and is paired with a monomer in the other strand, the Q monomer can have any base attached that would be complementary to the monomer in the corresponding paired position in the other strand.

Examples of nucleic acid monomers include non-natural, modified, and chemically-modified nucleotides, including any such nucleotides known in the art.

Examples of non-natural, modified, and chemically-modified nucleotide monomers include 2'-O-methyl ribonucleotides, 2'-O-methyl purine nucleotides, 2'-deoxy-2'-fluoro ribonucleotides, 2'-deoxy-2'-fluoro pyrimidine nucleotides, 2'-deoxy ribonucleotides, 2'-deoxy purine nucleotides, universal base nucleotides, 5-C-methyl-nucleotides, and inverted deoxyabasic monomer residues.

Examples of non-natural, modified, and chemically-modified nucleotide monomers include 3'-end stabilized nucleotides, 3'-glyceryl nucleotides, 3'-inverted abasic nucleotides, and 3'-inverted thymidine.

Examples of non-natural, modified, and chemically-modified nucleotide monomers include locked nucleic acid nucleotides (LNA), 2'-O, 4'-C-methylene-(D-ribofuranosyl) nucleotides, 2'-methoxyethoxy (MOE) nucleotides, 2'-methyl-thio-ethyl, 2'-deoxy-2'-fluoro nucleotides, and 2'-O-methyl nucleotides.

Examples of non-natural, modified, and chemically-modified nucleotide monomers include 2',4'-Constrained 2'-O-Methoxyethyl (cMOE) and 2'-O-Ethyl (cEt) modified DNAs.

Examples of non-natural, modified, and chemically-modified nucleotide monomers include 2'-amino nucleotides, 2'-O-amino nucleotides, 2'-C-allyl nucleotides, and 2'-O-allyl nucleotides.

Examples of non-natural, modified, and chemically-modified nucleotide monomers include $N^6$-methyladenosine nucleotides.

Examples of non-natural, modified, and chemically-modified nucleotide monomers include nucleotide monomers with modified bases 5-(3-amino)propyluridine, 5-(2-mercapto)ethyluridine, 5-bromouridine; 8-bromoguanosine, or 7-deazaadenosine.

Examples of non-natural, modified, and chemically-modified nucleotide monomers include 2'-O-aminopropyl substituted nucleotides.

Examples of non-natural, modified, and chemically-modified nucleotide monomers include replacing the 2'-OH group of a nucleotide with a 2'-R, a 2'-OR, a 2'-halogen, a 2'-SR, or a 2'-amino, where R can be H, alkyl, alkenyl, or alkynyl.

Some examples of modified nucleotides are given in Saenger, Principles of Nucleic Acid Structure, Springer-Verlag, 1984.

UNA Oligomeric Compounds Containing UNA Monomer Linkers

Aspects of this invention can provide structures and compositions for UNA-containing oligomeric compounds. The oligomeric agents may incorporate one or more UNA monomers. Oligomeric molecules of this invention can be used as active agents in formulations for gene regulating or gene silencing therapeutics.

An oligomer can be single stranded, or double stranded, or may have additional strands or non-strand structures.

In some embodiments, this invention provides oligomeric compounds having a structure that incorporates novel combinations of UNA monomers with certain natural nucleotides, non-natural nucleotides, modified nucleotides, or chemically-modified nucleotides.

In further aspects, the oligomeric compounds can be pharmacologically active molecules. A UNA oligomer of this invention can be used as an active pharmaceutical ingredient for regulating or modulating gene expression, and in RNA interference methods, as well as antisense, RNA blocking, and micro-RNA strategies.

A UNA oligomer of this invention can have the structure of Formula I

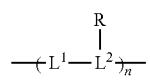

Formula I wherein $L^1$ is a linkage, n is from 19 to 29, and for each occurrence $L^2$ is a UNA linker group having the formula $-C^1-C^2-C^3-$, where R is attached to $C^2$ and has the formula $-OCH(CH_2R^3)R^5$, where $R^3$ is $-OR^4$, $-SR^4$, $-NR^4_2$, $-NH(C=O)R^4$, morpholino, morpholin-1-yl, piperazin-1-yl, or 4-alkanoyl-piperazin-1-yl, where $R^4$ is the same or different for each occurrence and is H, alkyl, a cholesterol, a lipid molecule, a polyamine, an amino acid, or a polypeptide, and where $R^5$ is a nucleobase, or $L^2(R)$ is a sugar such as a ribose and R is a nucleobase, or $L^2$ is a modified sugar such as a modified ribose and R is a nucleobase. In certain embodiments, a nucleobase can be a modified nucleobase. $L^1$ can be a phosphodiester linkage.

A UNA oligomer of this invention can be a short chain molecule. A UNA oligomer can be a duplex pair. Thus, a UNA oligomer can have a first strand of the duplex and a second strand of the duplex, which is complementary to the first strand, with respect to the nucleobases, although up to three mismatches can occur. A UNA oligomer duplex can have overhangs.

In some embodiments, a 3' overhang can be present on both strands, which can be 2 monomers in length. For example, a 3' overhang can be TT or uu.

Some UNA oligomers are discussed in U.S. Pat. No. 8,314,227, as well as US Patent Publication No. 20110313020 A1.

The target of a UNA oligomer can be a target nucleic acid. In some embodiments, the target can be any mRNA of a subject. A UNA oligomer can be active for gene silencing in RNA interference.

A UNA oligomer may comprise two strands that together provide a duplex. The duplex may be composed of a first strand, which may also be referred to as a passenger strand or sense strand, and a second strand, which may also be referred to as a guide strand or antisense strand.

In some aspects, a UNA oligomer of this invention can have any number of phosphorothioate intermonomer linkages in any position in any strand, or in both strands of a duplex structure.

In some embodiments, any one or more of the intermonomer linkages of a UNA oligomer can be a phosphodiester, a phosphorothioate including dithioates, a chiral phosphorothioate, and other chemically modified forms.

Examples of UNA oligomers of this invention include duplex pairs, which are in general complementary. Thus, for example, SEQ ID NO:1 can represent a first strand of a duplex and SEQ ID NO:2 can represent a second strand of the duplex, which is complementary to the first strand.

For example, the symbol "N" in the first strand can represent any nucleotide that is complementary to the monomer in the corresponding position in the second strand. Example UNA oligomers of this disclosure are shown with 2-monomer length overhangs, although overhangs of from 1 to 8 monomers, or longer, can be used.

The symbol "X" in a strand or oligomer represents a UNA monomer.

When a UNA monomer appears in one strand of the oligomer, and is unpaired with the other strand, the monomer can have any base attached. When a UNA monomer appears in one strand of the oligomer, and is paired with a monomer in the other strand, the UNA monomer can have any base attached that would be complementary to the monomer in the corresponding paired position in the other strand.

Further, when the oligomer terminates in a UNA monomer, the terminal position has a 1-end, according to the positional numbering shown above, instead of a 5'-end as for a nucleotide, or the terminal position has a 3-end, according to the positional numbering shown above, instead of a 3'-end as for a nucleotide. For example, the UNA oligomer

SEQ ID NO: 1
1-X-N-N-N-N-N-N-N-N-N-N-N-N-N-N-N-N-N-X-X-3

SEQ ID NO: 2
3-X-X-N-N-N-N-N-N-N-N-N-N-X-X-X-X-X-X-X-N-5' has a UNA monomer 1-end on the first strand, a UNA monomer 3-end on the first strand, a UNA monomer 3-end on the second strand, and a nucleotide 5'-end on the second strand.

In some embodiments, a UNA oligomer of this invention can have one or more UNA monomers at the 1-end of the first strand, and one or more UNA monomers at the 3-end of the first strand.

In further embodiments, a UNA oligomer of this invention can have one or more UNA monomers at the 3-end of the second strand.

In certain embodiments, a duplex UNA oligomer of this invention can have one or more UNA monomers at the 1-end of the first strand, one or more UNA monomers at the 3-end of the first strand, and one or more UNA monomers at the 3-end of the second strand.

A UNA oligomer of this invention the oligomer may have a first strand and a second strand, each of the strands independently being 19-23 monomers in length.

In certain embodiments, a UNA oligomer of this invention may have a first strand that is 19-23 monomers in length.

In certain embodiments, a UNA oligomer of this invention may have a duplex region that is 19-21 monomers in length.

In further embodiments, a UNA oligomer of this invention may have a second strand that is 19-23 monomers in length.

In certain embodiments, a UNA oligomer of this invention may have a first strand that is 19 monomers in length, and a second strand that is 21 monomers in length.

In certain embodiments, a UNA oligomer of this invention may have a first strand that is 20 monomers in length, and a second strand that is 21 monomers in length.

In certain embodiments, a UNA oligomer of this invention may have a first strand that is 21 monomers in length, and a second strand that is 21 monomers in length.

In certain embodiments, a UNA oligomer of this invention may have a first strand that is 22 monomers in length, and a second strand that is 21 monomers in length.

A UNA oligomer of this invention for inhibiting gene expression can have a first strand and a second strand, each of the strands being 19-29 monomers in length. The monomers can be UNA monomers and nucleic acid monomers. The oligomer can have a duplex structure of from 14 to 29 monomers in length. The UNA oligomer can be targeted to a target gene and can exhibit reduced off-target effects as compared to a conventional siRNA. In some embodiments, a UNA oligomer of this invention can have a first strand and a second strand, each of the strands being 19-23 monomers in length.

In another aspect, the UNA oligomer may have a blunt end, or may have one or more overhangs. In some embodiments, the first and second strands may be connected with a connecting oligomer in between the strands, and form a duplex region with a connecting loop at one end.

In certain embodiments, an overhang can be one or two monomers in length.

A UNA oligomer can mediate cleavage of a target nucleic acid in a cell. In some processes, the second strand of the UNA oligomer, at least a portion of which can be complementary to the target nucleic acid, can act as a guide strand that can hybridize to the target nucleic acid.

The second strand can be incorporated into an RNA Induced Silencing Complex (RISC).

A UNA oligomer of this disclosure may comprise naturally-occurring nucleic acid nucleotides, and modifications thereof that are compatible with gene silencing activity.

In some aspects, a UNA oligomer is a double stranded construct molecule that is able to inhibit gene expression.

As used herein, the term strand refers to a single, contiguous chain of monomers, the chain having any number of internal monomers and two end monomers, where each end monomer is attached to one internal monomer on one side, and is not attached to a monomer on the other side, so that it ends the chain.

The monomers of a UNA oligomer may be attached via phosphodiester linkages, phosphorothioate linkages, gapped linkages, and other variations.

In some embodiments, a UNA oligomer can include mismatches in complementarity between the first and second strands. In other embodiments, a UNA oligomer may have 1, or 2, or 3 mismatches. The mismatches may occur at any position in the duplex region.

The target of a UNA oligomer can be a target nucleic acid of a target gene.

A UNA oligomer may have one or two overhangs outside the duplex region. The overhangs can be an unpaired portion at the end of the first strand or second strand. The lengths of the overhang portions of the first and second strands can be the same or different.

A UNA oligomer may have at least one blunt end. A blunt end does not have an overhang portion, and the duplex region at a blunt end terminates at the same position for both the first and second strands.

A UNA oligomer can be RISC length, which means that it has a duplex length of less than 25 base pairs.

In certain embodiments, a UNA oligomer can be a single strand that folds upon itself and hybridizes to itself to form a double stranded region having a connecting loop at the end of the double stranded region.

Examples of UNA oligomers containing five UNA Monomers, and which may contain one or more Q monomers are shown in Table 1.

TABLE 1

5X UNA oligomers enriched in Q monomers

| SEQ ID NO: | OLIGOMER |
|---|---|
| 3 | X•Q•N•N•Q•N•Q•N•Q•Q•Q•N•Q•N•Q•N•Q•N•Q•N•X•X |
| 4 | X•X•Q•N•Q•N•Q•N•N•N•N•N•Q•N•Q•N•Q•N•Q•N•Q |
| 5 | X•Q•N•N•Q•N•Q•N•Q•N•Q•N•Q•N•Q•N•Q•N•Q•N•X•X |
| 6 | X•X•Q•N•Q•N•Q•N•Q•N•Q•N•Q•N•Q•N•Q•N•Q•N•Q |
| 7 | X•Q•N•N•Q•N•Q•N•N•N•N•N•Q•N•Q•N•Q•N•Q•N•X•X |
| 8 | X•X•Q•N•Q•N•Q•N•Q•N•N•N•Q•N•Q•N•Q•N•Q•N•Q |
| 9 | X•Q•N•N•Q•N•Q•N•N•N•N•N•Q•N•Q•N•Q•N•Q•N•X•X |
| 10 | X•X•Q•N•Q•N•Q•N•N•N•N•N•N•N•Q•N•Q•N•Q•N•Q |
| 11 | X•Q•N•N•Q•N•Q•N•N•N•N•N•N•N•Q•N•Q•N•Q•N•X•X |
| 12 | X•X•Q•N•Q•N•Q•N•N•N•N•N•N•N•N•N•Q•N•Q•N•Q |
| 13 | X•Q•N•N•Q•N•Q•N•N•N•N•N•N•N•N•Q•N•Q•N•X•X |
| 14 | X•X•Q•N•Q•N•Q•N•N•N•N•N•N•N•N•N•Q•N•Q•N•Q |
| 15 | X•Q•N•N•Q•N•Q•N•N•N•N•N•N•N•N•N•N•Q•N•Q•N•X•X |
| 16 | X•X•Q•N•Q•N•Q•N•N•N•N•N•N•N•N•N•N•N•Q•N•Q |
| 17 | X•Q•N•N•Q•N•N•N•N•N•N•N•N•N•N•N•Q•N•Q•N•X•X |
| 18 | X•X•Q•N•Q•N•Q•N•N•N•N•N•N•N•N•N•N•N•Q•N•Q |
| 19 | X•Q•N•N•Q•N•N•N•N•N•N•N•N•N•N•N•N•Q•N•Q•N•X•X |
| 20 | X•X•Q•N•Q•N•N•N•N•N•N•N•N•N•N•N•N•N•Q•N•Q |
| 21 | X•Q•N•N•N•N•N•N•N•N•N•N•N•N•N•N•Q•N•Q•N•X•X |
| 22 | X•X•Q•N•Q•N•N•N•N•N•N•N•N•N•N•N•N•N•Q•N•Q |
| 23 | X•Q•N•N•N•N•N•N•N•N•N•N•N•N•N•N•N•Q•N•Q•N•X•X |
| 24 | X•X•Q•N•Q•N•N•N•N•N•N•N•N•N•N•N•N•N•N•Q•N•Q |
| 25 | X•Q•N•N•N•N•N•N•N•N•N•N•N•N•N•N•N•N•Q•N•X•X |
| 26 | X•X•Q•N•N•N•N•N•N•N•N•N•N•N•N•N•N•N•N•Q•N•Q |
| 27 | X•Q•N•N•N•N•N•N•N•N•N•N•N•N•N•N•N•N•N•Q•N•X•X |
| 28 | X•X•Q•N•N•N•N•N•N•N•N•N•N•N•N•N•N•N•N•N•Q |
| 29 | X•Q•N•N•N•N•N•N•N•N•N•N•N•N•N•N•N•N•N•N•X•X |
| 30 | X•X•Q•N•N•N•N•N•N•N•N•N•N•N•N•N•N•N•N•N•Q |

Examples of UNA oligomers containing four UNA Monomers that are enriched in Q monomers are shown in Table 2.

TABLE 2

4X UNA oligomers enriched in Q monomers

| SEQ ID NO: | OLIGOMER |
|---|---|
| 31 | X•Q•N•N•Q•N•Q•N•Q•Q•Q•N•Q•N•Q•N•Q•N•Q•N•X•Q |
| 32 | X•X•Q•N•Q•N•Q•N•N•N•N•N•Q•N•Q•N•Q•N•Q•N•Q |
| 33 | X•Q•N•N•Q•N•Q•N•Q•N•Q•N•Q•N•Q•N•Q•N•Q•N•X•Q |
| 34 | X•X•Q•N•Q•N•Q•N•Q•N•Q•N•Q•N•Q•N•Q•N•Q•N•Q |
| 35 | X•Q•N•N•Q•N•Q•N•N•N•N•N•Q•N•Q•N•Q•N•Q•N•X•Q |
| 36 | X•X•Q•N•Q•N•Q•N•Q•N•N•N•Q•N•Q•N•Q•N•Q•N•Q |
| 37 | X•Q•N•N•Q•N•Q•N•N•N•N•N•Q•N•Q•N•Q•N•Q•N•X•Q |
| 38 | X•X•Q•N•Q•N•Q•N•N•N•N•N•N•N•Q•N•Q•N•Q•N•Q |
| 39 | X•Q•N•N•Q•N•Q•N•N•N•N•N•N•N•Q•N•Q•N•Q•N•X•Q |
| 40 | X•X•Q•N•Q•N•Q•N•N•N•N•N•N•N•N•N•Q•N•Q•N•Q |
| 41 | X•Q•N•N•Q•N•Q•N•N•N•N•N•N•N•N•Q•N•Q•N•X•Q |
| 42 | X•X•Q•N•Q•N•Q•N•N•N•N•N•N•N•N•N•Q•N•Q•N•Q |

TABLE 2-continued

4X UNA oligomers enriched in Q monomers

| SEQ ID NO: | OLIGOMER |
|---|---|
| 43 | X•Q•N•Q•N•Q•N•N•N•N•N•N•N•Q•N•Q•N•X•Q |
| 44 | X•X•Q•N•Q•N•Q•N•N•N•N•N•N•N•Q•N•Q |
| 45 | X•Q•N•Q•N•Q•N•N•N•N•N•N•N•Q•N•Q•N•X•Q |
| 46 | X•X•Q•N•Q•N•Q•N•N•N•N•N•N•N•N•Q•N•Q |
| 47 | X•Q•N•Q•N•Q•N•N•N•N•N•N•N•Q•N•Q•N•X•Q |
| 48 | X•X•Q•N•Q•N•N•N•N•N•N•N•N•N•Q•N•Q |
| 49 | X•Q•N•N•Q•N•N•N•N•N•N•N•N•Q•N•Q•N•X•Q |
| 50 | X•X•Q•N•Q•N•N•N•N•N•N•N•N•N•N•Q•N•Q |
| 51 | X•Q•N•N•N•N•N•N•N•N•N•N•N•N•N•Q•N•X•Q |
| 52 | X•X•Q•N•Q•N•N•N•N•N•N•N•N•N•N•N•Q•N•Q |
| 53 | X•Q•N•N•N•N•N•N•N•N•N•N•N•N•N•N•Q•N•X•Q |
| 54 | X•X•Q•N•N•N•N•N•N•N•N•N•N•N•N•N•Q•N•Q |
| 55 | X•Q•N•N•N•N•N•N•N•N•N•N•N•N•N•N•Q•N•X•Q |
| 56 | X•X•Q•N•N•N•N•N•N•N•N•N•N•N•N•N•N•N•Q |
| 57 | X•Q•N•N•N•N•N•N•N•N•N•N•N•N•N•N•N•X•Q |
| 58 | X•X•Q•N•N•N•N•N•N•N•N•N•N•N•N•N•N•N•Q |

Examples of UNA oligomers containing four UNA Monomers that are enriched in Q monomers are shown in Table 3.

TABLE 3

4X UNA oligomers enriched in Q monomers

| SEQ ID NO: | OLIGOMER |
|---|---|
| 59 | X•Q•N•Q•N•Q•N•Q•Q•Q•N•Q•N•Q•N•Q•N•X•X |
| 60 | Q•X•Q•N•Q•N•Q•N•Q•N•N•Q•N•Q•N•Q•N•Q |
| 61 | X•Q•N•Q•N•Q•N•Q•N•Q•N•Q•N•Q•N•Q•N•X•X |
| 62 | Q•X•Q•N•Q•N•Q•N•Q•N•Q•N•Q•N•Q•N•Q |
| 63 | X•Q•N•Q•N•Q•N•N•N•N•Q•N•Q•N•Q•N•X•X |
| 64 | Q•X•Q•N•Q•N•Q•N•Q•N•N•Q•N•Q•N•Q•N•Q |
| 65 | X•Q•N•Q•N•Q•N•N•N•N•Q•N•Q•N•Q•N•X•X |
| 66 | Q•X•Q•N•Q•N•Q•N•N•N•N•Q•N•Q•N•Q•N•Q |
| 67 | X•Q•N•Q•N•Q•N•N•N•N•N•N•Q•N•Q•N•Q•N•X•X |
| 68 | Q•X•Q•N•Q•N•Q•N•N•N•N•N•N•N•Q•N•Q•N•Q |
| 69 | X•Q•N•Q•N•Q•N•N•N•N•N•N•Q•N•Q•N•Q•N•X•X |
| 70 | Q•X•Q•N•Q•N•Q•N•N•N•N•N•N•N•Q•N•Q•N•Q |
| 71 | X•Q•N•Q•N•Q•N•N•N•N•N•N•N•Q•N•Q•N•X•X |
| 72 | Q•X•Q•N•Q•N•Q•N•Q•N•N•N•N•N•N•Q•N•Q•N•Q |
| 73 | X•Q•N•Q•N•N•N•N•N•N•N•N•N•N•Q•N•Q•N•X•X |
| 74 | Q•X•Q•N•Q•N•N•N•N•N•N•N•N•N•N•Q•N•Q•N•Q |
| 75 | X•Q•N•Q•N•N•N•N•N•N•N•N•N•N•Q•N•Q•N•X•X |
| 76 | Q•X•Q•N•Q•N•N•N•N•N•N•N•N•N•N•N•Q•N•Q |
| 77 | X•Q•N•N•N•N•N•N•N•N•N•N•N•Q•N•Q•N•X•X |
| 78 | Q•X•Q•N•Q•N•N•N•N•N•N•N•N•N•N•N•Q•N•Q |
| 79 | X•Q•N•N•N•N•N•N•N•N•N•N•N•N•N•Q•N•X•X |
| 80 | Q•X•Q•N•Q•N•N•N•N•N•N•N•N•N•N•N•N•Q•N•Q |
| 81 | X•Q•N•N•N•N•N•N•N•N•N•N•N•N•N•N•Q•N•X•X |
| 82 | Q•X•Q•N•N•N•N•N•N•N•N•N•N•N•N•N•Q•N•Q |
| 83 | X•Q•N•N•N•N•N•N•N•N•N•N•N•N•N•N•Q•N•X•X |
| 84 | Q•X•Q•N•N•N•N•N•N•N•N•N•N•N•N•N•N•N•Q |
| 85 | X•Q•N•N•N•N•N•N•N•N•N•N•N•N•N•N•N•X•X |
| 86 | Q•X•Q•N•N•N•N•N•N•N•N•N•N•N•N•N•N•N•Q |

Examples of UNA oligomers containing three UNA Monomers that are enriched in Q monomers are shown in Table 4.

TABLE 4

3X UNA oligomers enriched in Q monomers

| SEQ ID NO: | OLIGOMER |
|---|---|
| 87 | X•Q•N•Q•N•Q•N•Q•Q•Q•N•Q•N•Q•N•Q•N•X•Q |
| 88 | Q•X•Q•N•Q•N•Q•N•N•N•N•Q•N•Q•N•Q•N•Q |
| 89 | X•Q•N•Q•N•Q•N•Q•N•Q•N•Q•N•Q•N•Q•N•X•Q |
| 90 | Q•X•Q•N•Q•N•Q•N•Q•N•Q•N•Q•N•Q•N•Q |
| 91 | X•Q•N•Q•N•Q•N•N•N•N•Q•N•Q•N•Q•N•X•Q |
| 92 | Q•X•Q•N•Q•N•Q•N•Q•N•N•Q•N•Q•N•Q•N•Q |
| 93 | X•Q•N•Q•N•Q•N•N•N•N•Q•N•Q•N•Q•N•X•Q |
| 94 | Q•X•Q•N•Q•N•Q•N•N•N•N•Q•N•Q•N•Q•N•Q |
| 95 | X•Q•N•Q•N•Q•N•N•N•N•N•Q•N•Q•N•Q•N•X•Q |
| 96 | Q•X•Q•N•Q•N•Q•N•N•N•N•N•Q•N•Q•N•Q•N•Q |
| 97 | X•Q•N•Q•N•Q•N•N•N•N•N•N•Q•N•Q•N•X•Q |
| 98 | Q•X•Q•N•Q•N•Q•N•N•N•N•N•N•N•Q•N•Q•N•Q |
| 99 | X•Q•N•Q•N•Q•N•N•N•N•N•N•Q•N•Q•N•X•Q |
| 100 | Q•X•Q•N•Q•N•Q•N•N•N•N•N•N•N•N•Q•N•Q•N•Q |
| 101 | X•Q•N•Q•N•N•N•N•N•N•N•N•N•Q•N•Q•N•X•Q |
| 102 | Q•X•Q•N•Q•N•Q•N•N•N•N•N•N•N•N•N•Q•N•Q |
| 103 | X•Q•N•Q•N•N•N•N•N•N•N•N•N•Q•N•Q•N•X•Q |
| 104 | Q•X•Q•N•Q•N•N•N•N•N•N•N•N•N•N•Q•N•Q |
| 105 | X•Q•N•N•N•N•N•N•N•N•N•N•N•Q•N•Q•N•X•Q |
| 106 | Q•X•Q•N•Q•N•N•N•N•N•N•N•N•N•N•N•Q•N•Q |
| 107 | X•Q•N•N•N•N•N•N•N•N•N•N•N•N•Q•N•Q•N•X•Q |
| 108 | Q•X•Q•N•Q•N•N•N•N•N•N•N•N•N•N•N•Q•N•Q |
| 109 | X•Q•N•N•N•N•N•N•N•N•N•N•N•N•N•Q•N•X•Q |
| 110 | Q•X•Q•N•N•N•N•N•N•N•N•N•N•N•N•N•Q•N•Q |
| 111 | X•Q•N•N•N•N•N•N•N•N•N•N•N•N•N•N•Q•N•X•Q |
| 112 | Q•X•Q•N•N•N•N•N•N•N•N•N•N•N•N•N•N•Q |
| 113 | X•Q•N•N•N•N•N•N•N•N•N•N•N•N•N•N•N•X•Q |
| 114 | Q•X•Q•N•N•N•N•N•N•N•N•N•N•N•N•N•N•N•Q |

Examples of UNA oligomers containing six UNA Monomers that are enriched in Q monomers are shown in Table 5.

TABLE 5

6X UNA oligomers enriched in Q monomers

| SEQ ID NO: | OLIGOMER |
|---|---|
| 115 | X•Q•N•Q•N•Q•N•Q•Q•Q•N•Q•N•Q•N•Q•N•X•X |
| 116 | X•X•Q•N•Q•N•Q•N•N•N•N•Q•N•Q•N•Q•N•Q•X•Q |
| 117 | X•Q•N•Q•N•Q•N•Q•Q•Q•N•Q•N•Q•N•Q•N•X•X |
| 118 | X•X•Q•N•Q•N•Q•N•N•N•N•Q•N•Q•N•Q•N•X•N•Q |
| 119 | X•Q•N•Q•N•Q•N•Q•Q•Q•N•Q•N•Q•N•Q•N•X•X |
| 120 | X•X•Q•N•Q•N•Q•N•N•N•N•Q•N•Q•N•Q•X•Q•N•Q |
| 121 | X•Q•N•Q•N•Q•N•Q•Q•Q•N•Q•N•Q•N•Q•N•X•X |
| 122 | X•X•Q•N•Q•N•Q•N•N•N•N•Q•N•Q•N•X•N•Q•N•Q |
| 123 | X•Q•N•Q•N•Q•N•Q•Q•Q•N•Q•N•Q•N•Q•N•X•X |
| 124 | X•X•Q•N•Q•N•Q•N•N•N•N•Q•N•Q•X•Q•N•Q•N•Q |
| 125 | X•Q•N•Q•N•Q•N•Q•Q•Q•N•Q•N•Q•N•Q•N•X•X |
| 126 | X•X•Q•N•Q•N•Q•N•N•N•N•Q•N•X•N•Q•N•Q•N•Q |
| 127 | X•Q•N•Q•N•Q•N•Q•Q•Q•N•Q•N•Q•N•Q•N•X•X |
| 128 | X•X•Q•N•Q•N•Q•N•N•N•N•Q•X•Q•N•Q•N•Q•N•Q |

Examples of UNA oligomers containing seven UNA Monomers that are enriched in Q monomers are shown in Table 6.

TABLE 6

7X UNA oligomers enriched in Q monomers

| SEQ ID NO: | OLIGOMER |
|---|---|
| 129 | X•Q•N•Q•N•Q•N•Q•Q•Q•N•Q•N•Q•N•Q•N•X•X |
| 130 | X•X•Q•N•Q•N•Q•N•N•N•N•Q•N•Q•N•Q•N•X•X•Q |
| 131 | X•Q•N•Q•N•Q•N•Q•Q•Q•N•Q•N•Q•N•Q•N•X•X |
| 132 | X•X•Q•N•Q•N•Q•N•N•N•N•Q•N•Q•N•Q•X•Q•X•Q |
| 133 | X•Q•N•Q•N•Q•N•Q•Q•Q•N•Q•N•Q•N•Q•N•X•X |
| 134 | X•X•Q•N•Q•N•Q•N•N•N•N•Q•N•Q•N•X•N•Q•X•Q |
| 135 | X•Q•N•Q•N•Q•N•Q•Q•Q•N•Q•N•Q•N•Q•N•X•X |
| 136 | X•X•Q•N•Q•N•Q•N•N•N•N•Q•N•Q•X•Q•N•X•N•Q |
| 137 | X•Q•N•Q•N•Q•N•Q•Q•Q•N•Q•N•Q•N•Q•N•X•X |
| 138 | X•X•Q•N•Q•N•Q•N•N•N•N•Q•N•Q•X•X•Q•N•Q |
| 139 | X•Q•N•Q•N•Q•N•Q•Q•Q•N•Q•N•Q•N•Q•N•X•X |
| 140 | X•X•Q•N•Q•N•Q•N•N•N•N•Q•N•X•N•Q•X•Q•N•Q |
| 141 | X•Q•N•Q•N•Q•N•Q•Q•Q•N•Q•N•Q•N•Q•N•X•X |
| 142 | X•X•Q•N•Q•N•Q•N•N•N•N•Q•N•Q•X•X•N•Q•N•Q |

Examples of UNA oligomers containing five UNA Monomers that are enriched in Q monomers are shown in Table 7.

TABLE 7

5X UNA oligomers enriched in Q monomers

| SEQ ID NO: | OLIGOMER |
|---|---|
| 143 | X•Q•N•Q•N•Q•N•Q•Q•Q•N•Q•N•Q•N•Q•N•X•Q |
| 144 | X•X•Q•N•Q•N•Q•N•N•N•N•Q•N•Q•N•Q•N•Q•X•Q |
| 145 | X•Q•N•Q•N•Q•N•Q•Q•Q•N•Q•N•Q•N•Q•N•X•Q |
| 146 | X•X•Q•N•Q•N•Q•N•N•N•N•Q•N•Q•N•Q•N•X•N•Q |

TABLE 7-continued

5X UNA oligomers enriched in Q monomers

| SEQ ID NO: | OLIGOMER |
|---|---|
| 147 | X•Q•N•Q•N•Q•N•Q•Q•Q•N•Q•N•Q•N•Q•N•X•Q |
| 148 | X•X•Q•N•Q•N•Q•N•N•N•N•Q•N•Q•N•Q•X•Q•N•Q |
| 149 | X•Q•N•Q•N•Q•N•Q•Q•Q•N•Q•N•Q•N•Q•N•X•Q |
| 150 | X•X•Q•N•Q•N•Q•N•N•N•N•Q•N•Q•N•X•N•Q•N•Q |
| 151 | X•Q•N•Q•N•Q•N•Q•Q•Q•N•Q•N•Q•N•Q•N•X•Q |
| 152 | X•X•Q•N•Q•N•Q•N•N•N•N•Q•N•Q•X•Q•N•Q•N•Q |
| 153 | X•Q•N•Q•N•Q•N•Q•Q•Q•N•Q•N•Q•N•Q•N•X•Q |
| 154 | X•X•Q•N•Q•N•Q•N•N•N•N•Q•N•X•N•Q•N•Q•N•Q |
| 155 | X•Q•N•Q•N•Q•N•Q•Q•Q•N•Q•N•Q•N•Q•N•X•Q |
| 156 | X•X•Q•N•Q•N•Q•N•N•N•N•Q•X•Q•N•Q•N•Q•N•Q |

Examples of UNA oligomers containing six UNA Monomers that are enriched in Q monomers are shown in Table 8.

TABLE 8

6X UNA oligomers enriched in Q monomers

| SEQ ID NO: | OLIGOMER |
|---|---|
| 157 | X•Q•N•Q•N•Q•N•Q•Q•Q•N•Q•N•Q•N•Q•N•X•Q |
| 158 | X•X•Q•N•Q•N•Q•N•N•N•N•Q•N•Q•N•Q•N•X•X•Q |
| 159 | X•Q•N•Q•N•Q•N•Q•Q•Q•N•Q•N•Q•N•Q•N•X•Q |
| 160 | X•X•Q•N•Q•N•Q•N•N•N•N•Q•N•Q•N•Q•X•Q•X•Q |
| 161 | X•Q•N•Q•N•Q•N•Q•Q•Q•N•Q•N•Q•N•Q•N•X•Q |
| 162 | X•X•Q•N•Q•N•Q•N•N•N•N•Q•N•Q•N•X•N•Q•X•Q |
| 163 | X•Q•N•Q•N•Q•N•Q•Q•Q•N•Q•N•Q•N•Q•N•X•Q |
| 164 | X•X•Q•N•Q•N•Q•N•N•N•N•Q•N•Q•X•Q•N•X•N•Q |
| 165 | X•Q•N•Q•N•Q•N•Q•Q•Q•N•Q•N•Q•N•Q•N•X•Q |
| 166 | X•X•Q•N•Q•N•Q•N•N•N•N•Q•N•Q•N•X•X•Q•N•Q |
| 167 | X•Q•N•Q•N•Q•N•Q•Q•Q•N•Q•N•Q•N•Q•N•X•Q |
| 168 | X•X•Q•N•Q•N•Q•N•N•N•N•Q•N•X•N•Q•X•Q•N•Q |
| 169 | X•Q•N•Q•N•Q•N•Q•Q•Q•N•Q•N•Q•N•Q•N•X•Q |
| 170 | X•X•Q•N•Q•N•Q•N•N•N•N•Q•N•Q•X•X•N•Q•N•Q |

Examples of UNA oligomers containing five UNA Monomers that are enriched in Q monomers are shown in Table 9.

TABLE 9

5X UNA oligomers enriched in Q monomers

| SEQ ID NO: | OLIGOMER |
|---|---|
| 171 | X•Q•N•Q•N•Q•N•Q•Q•Q•N•Q•N•Q•N•Q•N•X•X |
| 172 | Q•X•Q•N•Q•N•Q•N•N•N•N•Q•N•Q•N•Q•N•Q•X•Q |
| 173 | X•Q•N•Q•N•Q•N•Q•Q•Q•N•Q•N•Q•N•Q•N•X•X |
| 174 | Q•X•Q•N•Q•N•Q•N•N•N•N•Q•N•Q•N•Q•N•X•N•Q |
| 175 | X•Q•N•Q•N•Q•N•Q•Q•Q•N•Q•N•Q•N•Q•N•X•X |
| 176 | Q•X•Q•N•Q•N•Q•N•N•N•N•Q•N•Q•N•Q•X•Q•N•Q |
| 177 | X•Q•N•Q•N•Q•N•Q•Q•Q•N•Q•N•Q•N•Q•N•X•X |
| 178 | Q•X•Q•N•Q•N•Q•N•N•N•N•Q•N•Q•N•X•N•Q•N•Q |

TABLE 9-continued

5X UNA oligomers enriched in Q monomers

| SEQ ID NO: | OLIGOMER |
|---|---|
| 179 | X•Q•N•Q•N•Q•N•Q•Q•Q•N•Q•N•Q•N•Q•N•X•X |
| 180 | Q•X•Q•N•Q•N•Q•N•N•N•N•Q•N•Q•X•Q•N•Q•N•Q |
| 181 | X•Q•N•Q•N•Q•N•Q•Q•Q•N•Q•N•Q•N•Q•N•X•X |
| 182 | Q•X•Q•N•Q•N•Q•N•N•N•N•Q•N•X•N•Q•N•Q•N•Q |
| 183 | X•Q•N•Q•N•Q•N•Q•Q•Q•N•Q•N•Q•N•Q•N•X•X |
| 184 | Q•X•Q•N•Q•N•Q•N•N•N•N•Q•N•X•Q•N•Q•N•Q•N•Q |

Examples of UNA oligomers containing six UNA Monomers that are enriched in Q monomers are shown in Table 10.

TABLE 10

6X UNA oligomers enriched in Q monomers

| SEQ ID NO: | OLIGOMER |
|---|---|
| 185 | X•Q•N•Q•N•Q•N•Q•Q•Q•N•Q•N•Q•N•Q•N•X•X |
| 186 | Q•X•Q•N•Q•N•Q•N•N•N•N•Q•N•Q•N•Q•N•X•X•Q |
| 187 | X•Q•N•Q•N•Q•N•Q•Q•Q•N•Q•N•Q•N•Q•N•X•X |
| 188 | Q•X•Q•N•Q•N•Q•N•N•N•N•Q•N•Q•N•Q•X•Q•X•Q |
| 189 | X•Q•N•Q•N•Q•N•Q•Q•Q•N•Q•N•Q•N•Q•N•X•X |
| 190 | Q•X•Q•N•Q•N•Q•N•N•N•N•Q•N•Q•N•X•N•Q•X•Q |
| 191 | X•Q•N•Q•N•Q•N•Q•Q•Q•N•Q•N•Q•N•Q•N•X•X |
| 192 | Q•X•Q•N•Q•N•Q•N•N•N•N•Q•N•Q•X•Q•N•X•N•Q |
| 193 | X•Q•N•Q•N•Q•N•Q•Q•Q•N•Q•N•Q•N•Q•N•X•X |
| 194 | Q•X•Q•N•Q•N•Q•N•N•N•N•Q•N•Q•N•X•X•Q•N•Q |
| 195 | X•Q•N•Q•N•Q•N•Q•Q•Q•N•Q•N•Q•N•Q•N•X•X |
| 196 | Q•X•Q•N•Q•N•Q•N•N•N•N•Q•N•X•N•Q•X•Q•N•Q |
| 197 | X•Q•N•Q•N•Q•N•Q•Q•Q•N•Q•N•Q•N•Q•N•X•X |
| 198 | Q•X•Q•N•Q•N•Q•N•N•N•N•Q•N•Q•X•N•Q•N•Q |

Examples of UNA oligomers containing four UNA Monomers that are enriched in Q monomers are shown in Table 11.

TABLE 11

4XUNA oligomers enriched in Q monomers

| SEQ ID NO: | OLIGOMER |
|---|---|
| 199 | X•Q•N•Q•N•Q•N•Q•Q•Q•N•Q•N•Q•N•Q•N•X•Q |
| 200 | Q•X•Q•N•Q•N•Q•N•N•N•N•Q•N•Q•N•Q•N•Q•X•Q |
| 201 | X•Q•N•Q•N•Q•N•Q•Q•Q•N•Q•N•Q•N•Q•N•X•Q |
| 202 | Q•X•Q•N•Q•N•Q•N•N•N•N•Q•N•Q•N•Q•N•X•N•Q |
| 203 | X•Q•N•Q•N•Q•N•Q•Q•Q•N•Q•N•Q•N•Q•N•X•Q |
| 204 | Q•X•Q•N•Q•N•Q•N•N•N•N•Q•N•Q•N•Q•X•Q•N•Q |
| 205 | X•Q•N•Q•N•Q•N•Q•Q•Q•N•Q•N•Q•N•Q•N•X•Q |
| 206 | Q•X•Q•N•Q•N•Q•N•N•N•N•Q•N•Q•N•X•Q•N•Q |
| 207 | X•Q•N•Q•N•Q•N•Q•Q•Q•N•Q•N•Q•N•Q•N•X•Q |
| 208 | Q•X•Q•N•Q•N•Q•N•N•N•N•Q•N•Q•X•Q•N•Q•N•Q |

TABLE 11-continued

4XUNA oligomers enriched in Q monomers

| SEQ ID NO: | OLIGOMER |
|---|---|
| 209 | X•Q•N•Q•N•Q•N•Q•Q•Q•N•Q•N•Q•N•Q•N•X•Q |
| 210 | Q•X•Q•N•Q•N•Q•N•N•N•N•Q•N•X•N•Q•N•Q•N•Q |
| 211 | X•Q•N•Q•N•Q•N•Q•Q•Q•N•Q•N•Q•N•Q•N•X•Q |
| 212 | Q•X•Q•N•Q•N•Q•N•N•N•N•Q•X•Q•N•Q•N•Q•N•Q |

Examples of UNA Oligomers containing five UNA Monomers that are enriched in Q monomers are shown in Table 12.

TABLE 12

5X UNA oligomers enriched in Q monomers

| SEQ ID NO: | OLIGOMER |
|---|---|
| 213 | X•Q•N•Q•N•Q•N•Q•Q•Q•N•Q•N•Q•N•Q•N•X•Q |
| 214 | Q•X•Q•N•Q•N•Q•N•N•N•N•Q•N•Q•N•Q•N•X•X•Q |
| 215 | X•Q•N•Q•N•Q•N•Q•Q•Q•N•Q•N•Q•N•Q•N•X•Q |
| 216 | Q•X•Q•N•Q•N•Q•N•N•N•N•Q•N•Q•N•Q•X•Q•X•Q |
| 217 | X•Q•N•Q•N•Q•N•Q•Q•Q•N•Q•N•Q•N•Q•N•X•Q |
| 218 | Q•X•Q•N•Q•N•Q•N•N•N•N•Q•N•Q•N•X•N•Q•X•Q |
| 219 | X•Q•N•Q•N•Q•N•Q•Q•Q•N•Q•N•Q•N•Q•N•X•Q |
| 220 | Q•X•Q•N•Q•N•Q•N•N•N•N•Q•N•Q•X•Q•N•X•N•Q |
| 221 | X•Q•N•Q•N•Q•N•Q•Q•Q•N•Q•N•Q•N•Q•N•X•Q |
| 222 | Q•X•Q•N•Q•N•Q•N•N•N•N•Q•N•Q•N•X•Q•N•Q |
| 223 | X•Q•N•Q•N•Q•N•Q•Q•Q•N•Q•N•Q•N•Q•N•X•Q |
| 224 | Q•X•Q•N•Q•N•Q•N•N•N•N•Q•N•X•N•Q•X•Q•N•Q |
| 225 | X•Q•N•Q•N•Q•N•Q•Q•Q•N•Q•N•Q•N•Q•N•X•Q |
| 226 | Q•X•Q•N•Q•N•Q•N•N•N•N•Q•N•Q•X•X•N•Q•N•Q |

Examples of UNA oligomers containing seven or more UNA Monomers that are enriched in Q monomers are shown in Table 13.

TABLE 13

7X-11X UNA oligomers enriched in Q monomers

| SEQ ID NO: | OLIGOMER |
|---|---|
| 227 | X•Q•N•Q•N•Q•N•Q•Q•Q•N•Q•N•Q•N•Q•N•X•X |
| 228 | X•X•Q•N•Q•N•Q•N•N•N•N•Q•N•Q•X•Q•X•Q•X•Q |
| 229 | X•Q•N•Q•N•Q•N•Q•Q•Q•N•Q•N•Q•N•Q•N•X•Q |
| 230 | X•X•Q•N•Q•N•Q•N•N•N•N•Q•N•Q•N•Q•X•X•X•Q |
| 231 | X•Q•N•Q•N•Q•N•Q•Q•Q•N•Q•N•Q•N•Q•N•X•X |
| 232 | Q•X•Q•N•Q•N•Q•N•N•N•N•Q•N•X•X•N•Q•N•Q |
| 233 | X•Q•N•Q•N•Q•N•Q•Q•Q•N•Q•N•Q•N•Q•N•X•Q |
| 234 | Q•X•Q•N•Q•N•Q•N•N•N•N•Q•N•X•X•X•X•X•Q |
| 235 | X•Q•N•Q•N•Q•N•Q•Q•Q•N•Q•N•Q•N•Q•N•X•X |
| 236 | X•X•Q•N•Q•N•Q•N•N•N•N•Q•N•X•X•X•X•X•X•Q |

The oligomeric structures shown in Tables 1 to 13 are double stranded structures, composed of a first strand (top) and a second strand (bottom). Each of the first and second strands is an oligomeric molecule that, by itself, can be a single stranded molecule. The single stranded molecules can be active for modulating gene expression.

An oligomeric compound of this invention may have any one of the structures shown in Tables 1 to 13. An oligomeric compound of this invention may have any one of the structures shown in Tables 1 to 13, where the structure has a nucleobase sequence targeted to a corresponding nucleic acid target.

An oligomeric compound of this invention may have any one of the sequences shown in Tables 1 to 13.

An oligomeric compound of this invention may be any one of the strands shown in Tables 1 to 13.

In some embodiments, an oligomeric compound of this invention may have a first strand and a second strand, each of the strands independently being 19-23 monomers in length, where any monomer that is not a UNA monomer can be a Q monomer.

In some embodiments, an oligomeric compound of this invention may have a first strand and a second strand, each of the strands independently being 19-23 monomers in length, where any monomer that is not a UNA monomer can be a Q monomer, and where the number of Q monomers is less than twenty.

In some embodiments, an oligomeric compound of this invention may have a first strand and a second strand, each of the strands independently being 19-23 monomers in length, where any monomer that is not a UNA monomer can be a Q monomer, and where the number of Q monomers is less than twelve.

In some embodiments, an oligomeric compound of this invention may have a first strand and a second strand, each of the strands independently being 19-23 monomers in length, where any monomer that is not a UNA monomer can be a Q monomer, and where the number of Q monomers is less than ten.

In some embodiments, an oligomeric compound of this invention may have a first strand and a second strand, each of the strands independently being 19-23 monomers in length, where any monomer that is not a UNA monomer can be a Q monomer, and where the number of Q monomers is less than eight.

In some embodiments, an oligomeric compound of this invention may have a first strand and a second strand, each of the strands independently being 19-23 monomers in length, where any monomer that is not a UNA monomer can be a Q monomer, and where the number of Q monomers is from 1 to 20.

In some embodiments, an oligomeric compound of this invention may have a first strand and a second strand, each of the strands independently being 19-23 monomers in length, where any monomer that is not a UNA monomer can be a Q monomer, and where the number of Q monomers is from 1 to 15.

In some embodiments, an oligomeric compound of this invention may have a first strand and a second strand, each of the strands independently being 19-23 monomers in length, where any monomer that is not a UNA monomer can be a Q monomer, and where the number of Q monomers is from 1 to 9.

In some embodiments, an oligomeric compound of this invention may have a first strand and a second strand, each of the strands independently being 19-23 monomers in length, where any monomer that is not a UNA monomer can be a 2'-O-Methyl modified ribonucleotide.

In some embodiments, an oligomeric compound of this invention may have a first strand and a second strand, each of the strands independently being 19-23 monomers in length, where any monomer that is not a UNA monomer can be a 2'-O-Methyl modified ribonucleotide, and where the number of 2'-O-Methyl modified ribonucleotides is less than twenty.

In some embodiments, an oligomeric compound of this invention may have a first strand and a second strand, each of the strands independently being 19-23 monomers in length, where any monomer that is not a UNA monomer can be a 2'-O-Methyl modified ribonucleotide, and where the number of 2'-O-Methyl modified ribonucleotides is less than twelve.

In some embodiments, an oligomeric compound of this invention may have a first strand and a second strand, each of the strands independently being 19-23 monomers in length, where any monomer that is not a UNA monomer can be a 2'-O-Methyl modified ribonucleotide, and where the number of 2'-O-Methyl modified ribonucleotides is less than ten.

In some embodiments, an oligomeric compound of this invention may have a first strand and a second strand, each of the strands independently being 19-23 monomers in length, where any monomer that is not a UNA monomer can be a 2'-O-Methyl modified ribonucleotide, and where the number of 2'-O-Methyl modified ribonucleotides is less than eight.

In some embodiments, an oligomeric compound of this invention may have a first strand and a second strand, each of the strands independently being 19-23 monomers in length, where any monomer that is not a UNA monomer can be a 2'-O-Methyl modified ribonucleotide, and where the number of 2'-O-Methyl modified ribonucleotides is from 1 to 20.

In some embodiments, an oligomeric compound of this invention may have a first strand and a second strand, each of the strands independently being 19-23 monomers in length, where any monomer that is not a UNA monomer can be a 2'-O-Methyl modified ribonucleotide, and where the number of 2'-O-Methyl modified ribonucleotides is from 1 to 15.

In some embodiments, an oligomeric compound of this invention may have a first strand and a second strand, each of the strands independently being 19-23 monomers in length, where any monomer that is not a UNA monomer can be a 2'-O-Methyl modified ribonucleotide, and where the number of 2'-O-Methyl modified ribonucleotides is from 1 to 9.

An oligomeric compound of this invention may be a single stranded molecule, wherein the single strand is any one of the strands shown in Tables 1 to 13.

In some embodiments, an oligomeric compound of this invention may have a single strand being 19-23 monomers in length, where any monomer that is not a UNA monomer can be a Q monomer.

In some embodiments, an oligomeric compound of this invention may have a single strand being 19-23 monomers in length, where any monomer that is not a UNA monomer can be a Q monomer, and where the number of Q monomers is less than twenty.

In some embodiments, an oligomeric compound of this invention may have a single strand being 19-23 monomers in length, where any monomer that is not a UNA monomer can be a Q monomer, and where the number of Q monomers is less than twelve.

In some embodiments, an oligomeric compound of this invention may have a single strand being 19-23 monomers in length, where any monomer that is not a UNA monomer can be a Q monomer, and where the number of Q monomers is less than ten.

In some embodiments, an oligomeric compound of this invention may have a single strand being 19-23 monomers in length, where any monomer that is not a UNA monomer can be a Q monomer, and where the number of Q monomers is less than eight.

In some embodiments, an oligomeric compound of this invention may have a single strand being 19-23 monomers in length, where any monomer that is not a UNA monomer can be a Q monomer, and where the number of Q monomers is from 1 to 20.

In some embodiments, an oligomeric compound of this invention may have a single strand being 19-23 monomers in length, where any monomer that is not a UNA monomer can be a Q monomer, and where the number of Q monomers is from 1 to 15.

In some embodiments, an oligomeric compound of this invention may have a single strand being 19-23 monomers in length, where any monomer that is not a UNA monomer can be a Q monomer, and where the number of Q monomers is from 1 to 9.

In some embodiments, an oligomeric compound of this invention may have a single strand being 19-23 monomers in length, where any monomer that is not a UNA monomer can be a 2'-O-Methyl modified ribonucleotide.

In some embodiments, an oligomeric compound of this invention may have a single strand being 19-23 monomers in length, where any monomer that is not a UNA monomer can be a 2'-O-Methyl modified ribonucleotide, and where the number of 2'-O-Methyl modified ribonucleotides is less than twenty.

In some embodiments, an oligomeric compound of this invention may have a single strand being 19-23 monomers in length, where any monomer that is not a UNA monomer can be a 2'-O-Methyl modified ribonucleotide, and where the number of 2'-O-Methyl modified ribonucleotides is less than twelve.

In some embodiments, an oligomeric compound of this invention may have a single strand being 19-23 monomers in length, where any monomer that is not a UNA monomer can be a 2'-O-Methyl modified ribonucleotide, and where the number of 2'-O-Methyl modified ribonucleotides is less than ten.

In some embodiments, an oligomeric compound of this invention may have a single strand being 19-23 monomers in length, where any monomer that is not a UNA monomer can be a 2'-O-Methyl modified ribonucleotide, and where the number of 2'-O-Methyl modified ribonucleotides is less than eight.

In some embodiments, an oligomeric compound of this invention may have a single strand being 19-23 monomers in length, where any monomer that is not a UNA monomer can be a 2'-O-Methyl modified ribonucleotide, and where the number of 2'-O-Methyl modified ribonucleotides is from 1 to 20.

In some embodiments, an oligomeric compound of this invention may have a single strand being 19-23 monomers in length, where any monomer that is not a UNA monomer can be a 2'-O-Methyl modified ribonucleotide, and where the number of 2'-O-Methyl modified ribonucleotides is from 1 to 15.

In some embodiments, an oligomeric compound of this invention may have a single strand being 19-23 monomers in length, where any monomer that is not a UNA monomer can be a 2'-O-Methyl modified ribonucleotide, and where the number of 2'-O-Methyl modified ribonucleotides is from 1 to 9.

Methods for Treating Disease

Methods of this invention include the treatment and prevention of various diseases in mammalian subjects. A subject can be human.

In the methods of this invention, a subject in need of treatment or prevention can be administered an effective amount of an oligomeric compound of this invention. A subject can be a human or mammal.

An effective amount of an oligomeric compound of this invention can be a dose ranging from 0.001 mg/kg to 50.0 mg/kg.

In the methods of this invention, target mRNA expression can be reduced in a subject for at least 5 days. In certain embodiments, target mRNA expression can be reduced in a subject for at least 10 days, or 15 days.

In the methods of this disclosure, the administration of an oligomeric compound of this invention may not result in an inflammatory response.

In further embodiments, this invention includes methods for inhibiting expression of a target gene in a cell, by treating the cell with an oligomeric compound of this invention.

In additional embodiments, this invention includes methods for inhibiting expression of a target gene in a mammal, by administering to the mammal a composition containing a UNA oligomer.

UNA Oligomers for TTR

Embodiments of this invention can provide oligomeric molecules that are active agents targeted to TTR.

Examples of UNA oligomers of this invention that are targeted to TTR are shown in Tables 14 to 17. Tables 14 and 15 represent "sense" and "antisense" pairs, and Tables 16 and 17 represent additional "sense" and "antisense" pairs. For example, SEQ ID Nos:237 and 238 are a sense and antisense pair.

TABLE 14

UNA oligomers targeted to TTR

| SEQ ID NO | Strand | UNA oligomers (5' - 3') |
|---|---|---|
| 237 | Sense | ŨmGrUmArAmCrCmArArGrAmGrUmArUmUrCmCrAŨmU |
| 238 | Anti | mUrGmGrAmArUmArCmUrCmUmUmGrGmUrUmArCmAŨmU |
| 239 | Sense | ŨmGrUmArAmCrCmArArGrAmGrUmArUmUrCmCrAŨmU |
| 240 | Anti | mUrGmGrAmArUmArCmUrCmUmUmGrGmUrUmArCmAŨmU |
| 241 | Sense | Ũ*mG*rUmArAmCrCmArArGrAmGrUmArUmUrCmCA*Ũ*mU |
| 242 | Anti | mU*G*mGrAmArUmArCmUrCmUmUmGrGmUrUmArCmA*Ũ*mU |
| 243 | Sense | Ũ*mG*U*mArAmCrCmArArGrAmGrUmArUmUrCmC*A*Ũ*mU |
| 244 | Anti | mU*G*mG*rAmArUmArCmUrCmUmUmGrGmUrUmAC*mA*Ũ*mU |
| 245 | Sense | Ũ*mG*2FU*mA2FAmC2FCmA2FA2FG2FAmG2FUmA2FUmU2FCmC*2FA*Ũ*2FU |

TABLE 14-continued

UNA oligomers targeted to TTR

| SEQ ID NO | Strand | UNA oligomers (5' - 3') |
|---|---|---|
| 246 | Anti | mU*2FG*mG*2FAmA2FUmA2FCmU2FCmUmUmG2FGmU2FUmA2FC*mA*Ũ*mU |
| 247 | Sense | Ğ*mG*U*mArAmCrCmArArGrAmGrUmArUrCmC*A*Ũ*mU |
| 248 | Anti | mU*G*mG*rAmArUmArCmUrCmUmUmGrGmUrUmAC*mU*Ũ*mU |

TABLE 15

UNA oligomers targeted to TTR

| SEQ ID NO | Strand | UNA oligomers (5' - 3') |
|---|---|---|
| 249 | Sense | ŨmGrUmArAmCrCArArGrAGrUArUUrCmCrAŨmU |
| 250 | Anti | mUrGmGrAArUArCUrCmUmUmGrGmUrUmArCCrAŨmU |
| 251 | Sense | ŨmGrUArACrCmArArGrAGrUArUmUrCCrAŨmU |
| 252 | Anti | mUrGmGrAArUArCmUrCUmUmGrGUrUArCmAŨmU |
| 253 | Sense | Ũ*G*rUmArAmCrCArArGrAGrUArUUrCCA*Ũ*mU |
| 254 | Anti | mU*G*mGrAmArUArCUrCUUGrGUrUmArCmA*Ũ*mU |
| 255 | Sense | Ũ*mG*U*mArACrCArArGrAGrUArUUrCC*A*Ũ*mU |
| 256 | Anti | mU*G*mG*rAmArUArCUrCUUGrGUrUAC*mA*Ũ*mU |
| 257 | Sense | Ũ*mG*2FU*mA2FAmC2FCmA2FA2FG2FAmG2FUmA2FUmU2FCmC*2FA*Ũ*2FU |
| 258 | Anti | mU*2FG*mG*2FAmA2FUmA2FCmU2FCmUmUmG2FGmU2FUmA2FC*mA*Ũ*mU |
| 259 | Sense | Ğ*mG*U*mArACrCArArGrAGrUArUUrCmC*A*Ũ*mU |
| 260 | Anti | mU*G*mG*rAArUArCUrCUUGrGUrUmAC*mU*Ũ*mU |

TABLE 16

UNA oligomers targeted to TTR

| SEQ ID NO | Strand | UNA oligomers (5' - 3') |
|---|---|---|
| 261 | Sense | ĞmArAmCrCmArAmGrArGrUmArUmUrCmCrAmUrUŨmU |
| 262 | Anti | mArAmUrGmGrAmArUArCmUmCmUrUmGrGmUrUmCŨmU |
| 263 | Sense | ĞmArAmCrCmArAmGrArGrUmArUmUrCmCrAmUrUŨmU |
| 264 | Anti | mArAmUrGmGrAmArUArCmUmCmUrUmGrGmUrUmCŨmU |
| 265 | Sense | Ğ*mA*rAmCrCmArAmGrArGrUmArUrCmCrAmUU*Ũ*mU |
| 266 | Anti | mA*A*mUrGmGrAmArUArCmUmCmUrUmGrGmUrUmC*Ũ*mU |
| 267 | Sense | Ğ*mA*A*mCrCmArAmGrArGrUmArUrCmCrAmU*U*Ũ*mU |
| 268 | Anti | mA*A*mU*rGmGrAmArUArCmUmCmUrUmGrGmUU*mC*Ũ*mU |
| 269 | Sense | Ğ*mA*2FA*mC2FCmA2FAmG2FA2FG2FUmA2FUmU2FCmC2FAmU*2FU*Ũ*2FU |
| 270 | Anti | mA*2FA*mU*2FGmG2FAmA2FUmA2FCmUmCmU2FUmG2FGmU2FU*mC*Ũ*mU |
| 271 | Sense | Č*mA*A*mCrCmArAmGrArGrUmArUrCmCrAmU*U*Ũ*mU |
| 272 | Anti | mA*A*mU*rGmGrAmArUArCmUmCmUrUmGrGmUU*mG*Ũ*mU |

TABLE 17

UNA oligomers targeted to TTR

| SEQ ID NO | Strand | UNA oligomers (5' - 3') |
|---|---|---|
| 273 | Sense | ĞmArAmCrCmArAGrArGrUArUUrCCrAmUrUŨmU |
| 274 | Anti | mArAmUrGmArAmUArCUCUrUmGrGmUrUmCŨmU |
| 275 | Sense | ĞmArAmCrCArAGrArGrUArUUrCCrAmUrUŨmU |
| 276 | Anti | mArAmUrGmGrAArUArCUCUrUmGrGmUrUmCŨmU |
| 277 | Sense | Ğ*mA*rAmCrCArAGrArGrUArUUrCCrAUU*Ũ*mU |
| 278 | Anti | mA*A*mUrGmGrAArUArCUCUrUmGrGmUrUmC*Ũ*mU |
| 279 | Sense | Ğ*mA*A*mCrCArAGrArGrUArUUrCCrAU*U*Ũ*mU |
| 280 | Anti | mA*A*mU*rGmGrAArUArCUCUrUmGrGUU*mC*Ũ*mU |
| 281 | Sense | Ğ*mA*2FA*mC2FCmA2FAmG2FA2FG2FUmA2FUmU2FCmC2FAmU*2FU*Ũ*2FU |
| 282 | Anti | mA*2FA*mU*2FGmG2FAmA2FUmA2FCmUmCmU2FUmG2FGmU2FU*mC*Ũ*mU |
| 283 | Sense | Č*mA*A*mCrCArAGrArGrUArUUrCCrAmU*U*Ũ*mU |
| 284 | Anti | mA*A*mU*rGGrAArUArCUmCmUrUGrGUU*G*Ũ*mU |

For example, a UNA oligomer may have a strand being SEQ ID NO:87. A UNA oligomer may have a strand being SEQ ID NO:88. A UNA oligomer may have a strand being SEQ ID NO:87, and a strand being SEQ ID NO:88. These UNA oligomers can have a nucleobase sequence corresponding to a target sequence of TTR. These UNA oligomers can have a nucleobase sequence corresponding to any of SEQ ID NOs:237 to 284.

For example, a UNA oligomer may have a strand being SEQ ID NO:105. A UNA oligomer may have a strand being SEQ ID NO:106. A UNA oligomer may have a strand being SEQ ID NO:105, and a strand being SEQ ID NO:106. These UNA oligomers can have a nucleobase sequence corresponding to a target sequence of TTR. These UNA oligomers can have a nucleobase sequence corresponding to any of SEQ ID NOs:237 to 284.

A UNA oligomer may comprise a first strand being SEQ ID NO:239 and a second strand being SEQ ID NO:240.

A UNA oligomer may comprise a first strand being SEQ ID NO:263 and a second strand being SEQ ID NO:264.

UNA Oligomers for APOB

Embodiments of this invention can provide oligomeric molecules that are active agents targeted to APOB.

Examples of UNA oligomers of this invention that are targeted to TTR are shown in Tables 18 and 19. Tables 18 and 19 represent "sense" and "antisense" pairs. For example, SEQ ID NOs:285 and 286 are a sense and antisense pair.

TABLE 18

UNA oligomers targeted to APOB

| SEQ ID NO | Strand | UNA oligomers (5' - 3') |
|---|---|---|
| 285 | Sense | rGrGrArArUrCrUrUrArUrArUrUrGrArUrCrCrArA |
| 286 | Anti | rUrUrGrGrArUrCrArArArUrArUrArArGrArUrUrCrC |
| 287 | Sense | G̃mGrAmArUmCrUmUrArUrAmUrUmUrGmArUmCrCmArAŨmU |
| 288 | Anti | mUrUmGrGmArUmCrAmArAmUmUrAmArGmArUmUrCmCŨmU |
| 289 | Sense | rGrGrArArUrCmUmUrAmUrAmUmUrGrArUrCmCrArAŨmU |
| 290 | Anti | mUrUmGrGrArUmCrArArAmUrAmUrArArGrAmUrUrCmCŨmU |
| 291 | Sense | rGrGrArArUrCmUmUrAmUrAmUmUrGrArUrCmCrArAŨmU |
| 292 | Anti | mUrUmGrGmArUmCrAmArAmUmUrAmArGmArUmUrCmCŨmU |
| 293 | Sense | G̃mGrAmArUmCrUmUrArUrAmUrUmUrGmArUmCrCmArAŨmU |
| 294 | Anti | mUrUmGrGrArUmCrArArAmUrAmUrArArGrAmUrUrCmCŨmU |

TABLE 19

UNA oligomers targeted to APOB

| SEQ ID NO | Strand | UNA oligomers (5' - 3') |
|---|---|---|
| 295 | Sense | rGrGrArArUrCrUrUrArUrArUrUrGrArUrCrCrArA |
| 296 | Anti | rUrUrGrGrArUrCrArArArUrArUrArArGrArUrUrCrC |
| 297 | Sense | G̃mGrAmArUmCrUUrArUrAUrUUrGArUCrCmArAŨmU |
| 298 | Anti | mUrUmGrGmArUmCrAArAUAUrAArGmArUmUrCmCŨmU |
| 299 | Sense | rGrGrArArUrCmUmUrAmUrAUUUrGrArUrCCrArAŨmU |
| 300 | Anti | mUmUrGrGrArUmCrArArAUrAmUrArArGrAmUrUrCmCŨmU |
| 301 | Sense | rGrGrArArUrCmUmUrAUrAUUUrGrArUrCCrArAŨmU |
| 302 | Anti | mUrUmGrGmArUCrAArAUAUrAArGArUmUrCmCŨmU |
| 303 | Sense | G̃mGrAmArUCrUUrArUrAUrUUrGArUCrCArAŨmU |
| 304 | Anti | mUmUrGrGrArUCrArArAUrAUrArArGrAmUrUrCmCŨmU |

For example, a UNA oligomer may have a strand being SEQ ID NO:87. A UNA oligomer may have a strand being SEQ ID NO:88. A UNA oligomer may have a strand being SEQ ID NO:87, and a strand being SEQ ID NO:88. These UNA oligomers can have a nucleobase sequence corresponding to a target sequence of APOB. These UNA oligomers can have a nucleobase sequence corresponding to any of SEQ ID NOs:285 to 304.

For example, a UNA oligomer may have a strand being SEQ ID NO:105. A UNA oligomer may have a strand being SEQ ID NO:106. A UNA oligomer may have a strand being SEQ ID NO:105, and a strand being SEQ ID NO:106. These UNA oligomers can have a nucleobase sequence corresponding to a target sequence of APOB. These UNA oligomers can have a nucleobase sequence corresponding to any of SEQ ID NOs:285 to 304.

A UNA oligomer may comprise a first strand being SEQ ID NO:287 and a second strand being SEQ ID NO:288.

A UNA oligomer may comprise a first strand being SEQ ID NO:291 and a second strand being SEQ ID NO:292.

UNA Oligomers for PCSK9.

Embodiments of this invention can provide oligomeric molecules that are active agents targeted to PCSK9.

Examples of UNA oligomers of this invention that are targeted to PCSK9 are shown in Tables 20 and 21. Tables 20 and 21 represent "sense" and "antisense" pairs. For example, SEQ ID NOs:305 and 306 are a sense and antisense pair.

TABLE 20

UNA oligomers targeted to PCSK9

| SEQ ID NO | Strand | UNA oligomers (5' - 3') |
|---|---|---|
| 305 | Sense | ḠmCrCmUrGmGrAmGrUrUmArUmUrCmGrGmArAŨmU |
| 306 | Anti | mUrUmCrCmGrAmArUmArAmAmCmUrCmCrAmGrGmCŨmU |
| 307 | Sense | ḠmCmUrGrGrArGmUmUmUrAmUmUrCrGrArAŨmU |
| 308 | Anti | mUrUmCrCmGrAmArUmArAmAmCmUrCmCrAmGrGmCŨmU |
| 309 | Sense | ḠrGrCrCrUrGrGrArGrUrUrUrArUrUrCrGrGrArAŨmU |
| 310 | Anti | rUrUrCrCrGrArArUrArArArCrUrCrCrArGrGrCŨmU |

TABLE 21

UNA oligomers targeted to PCSK9

| SEQ ID NO | Strand | UNA oligomers (5' - 3') |
|---|---|---|
| 311 | Sense | ḠmCrCmUrGmGrAGrUrUrUArUUrCGrGmArAŨmU |
| 312 | Anti | mUrUmCrCmGrAmArUArAACrUrCmCrAmGrGmCŨmU |
| 313 | Sense | ḠmCmCUrGrGrArGUUUrAUUmCrGrGrArAŨmU |
| 314 | Anti | mUrUmCrCmGrAArUArAACrUrCmCrAmGrGmCŨmU |
| 315 | Sense | ḠmGrCmCrUrGrGrArGrUrUrUrArUrUrCrGrGrArAŨmU |
| 316 | Anti | rUmUrCrCrGrArAmUmAmAmArCrUrCrCrArGrGrCŨmU |

For example, a UNA oligomer may have a strand being SEQ ID NO:87. A UNA oligomer may have a strand being SEQ ID NO:88. A UNA oligomer may have a strand being SEQ ID NO:87, and a strand being SEQ ID NO:88. These UNA oligomers can have a nucleobase sequence corresponding to a target sequence of PCSK9. These UNA oligomers can have a nucleobase sequence corresponding to any of SEQ ID NOs:305 to 316.

For example, a UNA oligomer may have a strand being SEQ ID NO:105. A UNA oligomer may have a strand being SEQ ID NO:106. A UNA oligomer may have a strand being SEQ ID NO:105, and a strand being SEQ ID NO:106. These UNA oligomers can have a nucleobase sequence corresponding to a target sequence of PCSK9. These UNA oligomers can have a nucleobase sequence corresponding to any of SEQ ID NOs:305 to 316.

A UNA oligomer may comprise a first strand being SEQ ID NO:305 and a second strand being SEQ ID NO:306.

UNA Oligomers for APOC3.

Embodiments of this invention can provide oligomeric molecules that are active agents targeted to APOC3.

Examples of UNA oligomers of this invention that are targeted to APOCIII are shown in Tables 22 and 23. Tables 22 and 23 represent "sense" and "antisense" pairs. For example, SEQ ID NOs:317 and 318 are a sense and antisense pair.

TABLE 22

UNA oligomers targeted to APOC3

| SEQ ID NO | Strand | UNA oligomers (5' - 3') |
|---|---|---|
| 317 | Sense | ÃrArArArGrGrArCrArGrUrArUrUrCrUrCrAŨmU |
| 318 | Anti | rUrGrArGrArArUrArCrUrGrUrCrCrCrUrUrUrUŨmU |
| 319 | Sense | Ã*mArAmArGmGrGmArCrArGmUrAmUrUmCrUmCrAŨ*mU |
| 320 | Anti | mU*rGmArGmArAmUrAmCrUmGmUmCrCmCrUmUrUmUŨ*mU |
| 321 | Sense | ÃmArAmArGmGrGmArCrArGmUrAmUrUmCrUmCrAŨmU |
| 322 | Anti | mUrGmArGmArAmUrAmCrUrGrUrCrCmCrUmUrUmUŨmU |
| 323 | Sense | Ã*mArAmArGmGrGmArCrArGmUrAmUrUmCrUmCrAŨ*mU |
| 324 | Anti | mU*rGmArGmArAmUrAmCrUrGrUrCrCmCrUmUrUmUŨ*mU |

TABLE 23

UNA oligomers targeted to APOC3

| SEQ ID NO | Strand | UNA oligomers (5' - 3') |
|---|---|---|
| 325 | Sense | ÃrArArArGrGrArCrArGrUrArUrUrCrUrCrAŨmU |
| 326 | Anti | rUrGrArGrArArUrArCrUrGrUrCrCrCrUrUrUrUŨmU |
| 327 | Sense | Ã*mArAmArGmGrGArCrArGUrAUrUCrUmCrAŨ*mU |
| 328 | Anti | mU*rGmArGmArAmUrACrUGUCrCmCrUmUrUmUŨ*mU |
| 329 | Sense | ÃmArAmArGGrGArCrArGUrAUrUCrUmCrAŨmU |
| 330 | Anti | mUrGmArGmArAmUrACrUrGrUrCrCCrUmUrUmUŨmU |
| 331 | Sense | Ã*mArAmArGGrGArCrArGUrAUrUCrUCrAŨ*mU |
| 332 | Anti | mU*rGmArGmArAUrACrUrGrUrCrCCrUmUrUmUŨ*mU |

For example, a UNA oligomer may have a strand being SEQ ID NO:87. A UNA oligomer may have a strand being SEQ ID NO:88. A UNA oligomer may have a strand being SEQ ID NO:87, and a strand being SEQ ID NO:88. These UNA oligomers can have a nucleobase sequence corresponding to a target sequence of APOC3. These UNA oligomers can have a nucleobase sequence corresponding to any of SEQ ID NOs:317 to 332.

For example, a UNA oligomer may have a strand being SEQ ID NO:105. A UNA oligomer may have a strand being SEQ ID NO:106. A UNA oligomer may have a strand being SEQ ID NO:105, and a strand being SEQ ID NO:106. These UNA oligomers can have a nucleobase sequence corresponding to a target sequence of APOC3. These UNA oligomers can have a nucleobase sequence corresponding to any of SEQ ID NOs:317 to 332.

A UNA oligomer may comprise a first strand being SEQ ID NO:319 and a second strand being SEQ ID NO:320.

A UNA oligomer may comprise a first strand being SEQ ID NO:321 and a second strand being SEQ ID NO:322.

UNA Oligomers for HBV

Embodiments of this invention can provide oligomeric molecules that are active agents targeted to HBV.

Examples of UNA oligomers of this invention that are targeted to HBV are shown in Tables 24 to 27. Tables 24 and 25 represent "sense" and "antisense" pairs, and Tables 26 and 27 represent additional "sense" and "antisense" pairs. For example, SEQ ID NOs:333 and 353 are a sense and antisense pair, and so on through SEQ ID NOs:352 and 372.

TABLE 24

UNA oligomers targeted to HBV (Sense)

| REF POS | SEQ ID NO | Sense (5'-3') SEQ ID NOS: 861 to 880 |
|---|---|---|
| 1525 | 333 | UNA-C/mGCmACmCUmCUCUmUUmACmGCmGG/ UNA-U/mU |
| 251 | 334 | UNA-G/mACmUCmGUmGGUGmGAmCUmUCmUC/ UNA-U/mU |
| 254 | 335 | UNA-U/mCGmUGmGUmGGACmUUmCUmCUmCA/ UNA-U/mU |
| 374 | 336 | UNA-U/mGGmAUmGUmGUCUmGCmGGmCGmUU/ UNA-U/mU |
| 1575 | 337 | UNA-C/mCGmUGmUGmCACUmUCmGCmUUmCA/ UNA-U/mU |
| 1577 | 338 | UNA-G/mUGmUGmCAmCUUCmGCmUUmCAmCC/ UNA-U/mU |
| 1578 | 339 | UNA-U/mGUmGCmACmUUCGmCUmUCmACmCU/ UNA-U/mU |
| 1579 | 340 | UNA-G/mUGmCAmCUmUCGCmUUmCAmCCmUC/ UNA-U/mU |
| 1581 | 341 | UNA-G/mCAmCUmUCmGCUUmCAmCCmUCmUG/ UNA-U/mU |
| 247 | 342 | UNA-U/mCUmAGmACmUCGUmGGmUGmGAmCU/ UNA-U/mU |
| 248 | 343 | UNA-C/mUAmGAmCUmCGUGmUGmGGmACmUU/ UNA-U/mU |
| 249 | 344 | UNA-U/mAGmACmUCmGUGGmUGmGAmCUmUC/ UNA-U/mU |
| 250 | 345 | UNA-A/mGAmCUmCGmUGGUmGGmACmUUmCU/ UNA-U/mU |
| 1776 | 346 | UNA-G/mGAmGGmCUmGUAGmGCmAUmAAmAU/ UNA-U/mU |
| 1777 | 347 | UNA-G/mAGmCmUGmUAGGmCAmUAmAAmUU/ UNA-U/mU |
| 1779 | 348 | UNA-G/mGCmUGmUAmGGCAmUAmAAmUUmGG/ UNA-U/mU |
| 1780 | 349 | UNA-G/mCUmGUmAGmGCAUmAAmAUmUGmGU/ UNA-U/mU |

TABLE 24-continued

UNA oligomers targeted to HBV (Sense)

| REF POS | SEQ ID NO | Sense (5'-3') SEQ ID NOS: 861 to 880 |
|---|---|---|
| 1781 | 350 | UNA-C/mUGmUAmGGmCAUAmAAmUUmGGmUC/ UNA-U/mU |
| 1782 | 351 | UNA-U/mGUmAGmGCmAUAAmAUmUGmGUmCU/ UNA-U/mU |
| 256 | 352 | UNA-G/mUGmGUmGGmACUUmCUmCUmCAmAU/ UNA-U/mU |

TABLE 25

UNA oligomers targeted to HBV (Antisense)

| REF POS | SEQ ID NO | Antisense (5'-3') SEQ ID NOS: 881 to 900 |
|---|---|---|
| 1525 | 353 | mCCmGCmGUmAAmAGmAmGmAGmGUmGCmG/ UNA-U/mU |
| 251 | 354 | mGAmGAmAGmUCmACmCmCmACmGAmGUmC/ UNA-U/mU |
| 254 | 355 | mUGmAGmAGmAAmGUmCmCmACmCAmCGmA/ UNA-U/mU |
| 374 | 356 | mAAmCGmCCmGCmAGmAmCmACmAUmCCmA/ UNA-U/mU |
| 1575 | 357 | mUGmAAmGCmGAmAGmUmGmCAmCAmCGmG/ UNA-U/mU |
| 1577 | 358 | mGGmUGmAAmGCmGAmAmGmUGmCAmCAmC/ UNA-U/mU |
| 1578 | 359 | mAGmGUmGAmAGmCGmAmAmGUmGCmACmA/ UNA-U/mU |
| 1579 | 360 | mGAmGGmUGmAAmGCmGmAmAGmUGmCAmC/ UNA-U/mU |
| 1581 | 361 | mCAmGAmGGmUGmAAmGCmGAmAGmUGmC/ UNA-U/mU |
| 247 | 362 | mAGmUCmCAmCCmACmGmAmGUmCUmAGmA/ UNA-U/mU |
| 248 | 363 | mAAmGUmCCmACmCAmCmGmAGmUCmUAmG/ UNA-U/mU |
| 249 | 364 | mGAmAGmUCmCAmCCmAmCmGAmGUmCUmA/ UNA-U/mU |
| 250 | 365 | mAGmAAmGUmCCmACmCmAmCGmAGmUCmU/ UNA-U/mU |
| 1776 | 366 | mAUmUUmAUmGCmCUmAmCmAGmCCmUCmC/ UNA-U/mU |
| 1777 | 367 | mAAmUUmUAmUGmCCmUmAmCAmGCmCUmC/ UNA-U/mU |
| 1779 | 368 | mCCmAAmUUmUAmUGmCmCmUAmCAmGCmC/ UNA-U/mU |
| 1780 | 369 | mACmCAmAUmUUmAUmGmCmCUmACmAGmC/ UNA-U/mU |
| 1781 | 370 | mGAmCCmAAmUUmUAmUmGmCCmUAmCAmG/ UNA-U/mU |

TABLE 25-continued

UNA oligomers targeted to HBV (Antisense)

| REF POS | SEQ ID NO | Antisense (5'-3') SEQ ID NOS: 881 to 900 |
|---|---|---|
| 1782 | 371 | mAGmACmCAmAUmUUmAmUmGCmCUmACmA/UNA-U/mU |
| 256 | 372 | mAUmUGmAGmAGmAAmGmUmCCmACmCAmC/UNA-U/mU |

TABLE 26

UNA oligomers targeted to HBV (Sense)

| REF POS | SEQ ID NO | Sense (5'-3') SEQ ID NOS: 901 to 921 |
|---|---|---|
| 1863 | 373 | UNA-U/mUCmAAmGCmCmCUCCmAAmGCmUGmUG/UNA-U/mU |
| 1864 | 374 | UNA-U/mCAmAGmCCmUCCAmAGmCUmGmUGmC/UNA-U/mU |
| 1865 | 375 | UNA-C/mAAmGCmCUmCCAAmGCmUGmUGmCC/UNA-U/mU |
| 1866 | 376 | UNA-A/mAGmCCmUCmCAAGmCUmGUmGCmCU/UNA-U/mU |
| 376 | 377 | UNA-G/mAUmGUmGUmCUGCmGGmCGmUUmUU/UNA-U/mU |
| 378 | 378 | UNA-U/mGUmGUmCUmGCGGmCGmUUmUUmAU/UNA-U/mU |
| 380 | 379 | UNA-U/mGUmCUmGCmGGCGmUUmUUmAUmCA/UNA-U/mU |
| 1818 | 380 | UNA-A/mACmUUmUUmUCACmCUmCUmGCmCU/UNA-U/mU |
| 244 | 381 | UNA-G/mAGmUCmUAmGACUmCGmUGmGUmGG/UNA-U/mU |
| 245 | 382 | UNA-A/mGUmCUmAGmACUCmGUmGGmUGmGA/UNA-U/mU |
| 246 | 383 | UNA-G/mUCmUAmGAmCUCGmUGmGUmGGmAC/UNA-U/mU |
| 409 | 384 | UNA-C/mAUmCCmUGmCUGCmUAmUGmCCmUC/UNA-U/mU |
| 411 | 385 | UNA-U/mCCmUGmCUmGCUAmUGmCCmUCmAU/UNA-U/mU |
| 412 | 386 | UNA-C/mCUmGCmUGmCUAUmGCmCUmCAmUC/UNA-U/mU |
| 413 | 387 | UNA-C/mUGmCUmGCmUAUGmCCmUCmAUmCU/UNA-U/mU |
| 414 | 388 | UNA-U/mGCmUGmCUmAUGCmCUmCAmUCmUU/UNA-U/mU |
| 252 | 389 | UNA-A/mCUmCGmUGmGUGGmACmUUmCUmCU/UNA-U/mU |
| 253 | 390 | UNA-C/mUCmGUmGGmUGGAmCUmUCmUCmUC/UNA-U/mU |
| 1576 | 391 | UNA-C/mGUmGUmGCmACUUmCGmCUmUCmAC/UNA-U/mU |
| 1580 | 392 | UNA-U/mGCmACmUUmCGCUmCUmCACmCmCUmCU/UNA-U/mU |

TABLE 26-continued

UNA oligomers targeted to HBV (Sense)

| REF POS | SEQ ID NO | Sense (5'-3') SEQ ID NOS: 901 to 921 |
|---|---|---|
| 1582 | 393 | UNA-C/mACmUUmCGmCUUCmACmCUmCUmGC/UNA-U/mU |

TABLE 27

UNA oligomers targeted to HBV (Antisense)

| REF POS | SEQ ID NO | Antisense (5'-3') SEQ ID NOS: 922 to 942 |
|---|---|---|
| 1863 | 394 | mCAmCAmGCmUUmGGmAmGmGCmUUmGAmA/UNA-U/mU |
| 1864 | 395 | mGCmACmAGmCUmGmGmAmGGmCUmGAmA/UNA-U/mU |
| 1865 | 396 | mGGmCAmCAmGCmUUmGmGmAGmGCmUUmG/UNA-U/mU |
| 1866 | 397 | mAGmGCmACmAGmCUmUmGmAGmGmCUmU/UNA-U/mU |
| 376 | 398 | mAAmAAmCGmCCmGCmAmGmACmACmAUmC/UNA-U/mU |
| 378 | 399 | mAUmAAmAAmCGmCCmGCmAGmAmCAmCmA/UNA-U/mU |
| 380 | 400 | mUGmAUmAAmAAmCGmCmCmGCmAGmACmA/UNA-U/mU |
| 1818 | 401 | mAGmGCmAGmAGmGUmGmAmAAmAAmGUmU/UNA-U/mU |
| 244 | 402 | mCCmACmCAmCGmAGmUCmUAmGAmCUmC/UNA-U/mU |
| 245 | 403 | mUCmCAmCCmACmGAmGUmCUmAGmACmU/UNA-U/mU |
| 246 | 404 | mGUmCCmACmCAmCGmAGmUCmUAmGAmC/UNA-U/mU |
| 409 | 405 | mGAmGGmCAmUAmGCmAGmCAmGGmAUmG/UNA-U/mU |
| 411 | 406 | mAUmGAmGGmCAmUAmGCmAGmCAmGGmA/UNA-U/mU |
| 412 | 407 | mGAmUGmAGmGCmAUmAmGCmAGmCAmGmG/UNA-U/mU |
| 413 | 408 | mAGmAUmGAmGGmCAmUmAmGCmAGmCAmG/UNA-U/mU |
| 414 | 409 | mAAmGAmUGmAGmGCmAmUmAGmCAmGCmA/UNA-U/mU |
| 252 | 410 | mAGmAGmAAmGUmCCmAmCmCAmCGmAGmU/UNA-U/mU |
| 253 | 411 | mGAmGAmGAmAGmUCmCmAmCCmACmGAmG/UNA-U/mU |
| 1576 | 412 | mGUmGAmAGmCGmAAmGmUmGCmACmACmG/UNA-U/mU |
| 1580 | 413 | mAGmAGmGUmGAmAGmCmGmAAmGUmGCmA/UNA-U/mU |

TABLE 27-continued

UNA oligomers targeted to HBV (Antisense)

| REF POS | SEQ ID NO | Antisense (5'-3') SEQ ID NOS: 922 to 942 |
|---|---|---|
| 1582 | 414 | mGCmAGmAGmGUmGAmAmGmCGmAAmGUmG/ UNA-U/mU |

For example, a UNA oligomer may have a strand being SEQ ID NO:87. A UNA oligomer may have a strand being SEQ ID NO:88. A UNA oligomer may have a strand being SEQ ID NO:87, and a strand being SEQ ID NO:88. These UNA oligomers can have a nucleobase sequence corresponding to a target sequence of a viral gene of Hepatitis B virus (HBV). These UNA oligomers can have a nucleobase sequence corresponding to any of SEQ ID NOs:333 to 414.

For example, a UNA oligomer may have a strand being SEQ ID NO:105. A UNA oligomer may have a strand being SEQ ID NO:106. A UNA oligomer may have a strand being SEQ ID NO:105, and a strand being SEQ ID NO:106. These UNA oligomers can have a nucleobase sequence corresponding to a target sequence of a viral gene of Hepatitis B virus (HBV). These UNA oligomers can have a nucleobase sequence corresponding to any of SEQ ID NOs: 333 to 414.

Methods for Treating Disease

Methods of this invention include the treatment and prevention of various diseases in mammalian subjects. A subject can be a human or mammal.

In the methods of this invention, a subject in need of treatment or prevention can be administered an effective amount of an oligomeric compound of this invention.

In addition, the UNA oligomers of this invention may provide increased activity in vitro, as well as increased potency in vivo.

Further, the UNA oligomers of this invention may provide increased enzymatic stability.

Moreover, the UNA oligomers of this invention can provide long lasting activity in vitro, as well as long lasting potency in vivo.

A UNA oligomer of this invention can retain at least 50% activity in vitro six days after transfection.

A UNA oligomer of this invention can retain at least 80% activity in vitro six days after transfection.

A UNA oligomer of this invention can retain at least 30% potency in vivo six days after administration.

A UNA oligomer of this invention can retain at least 50% potency in vivo six days after administration.

UNA oligomers of this invention can provide long acting properties, and reduce the dose levels required for efficacious therapy.

An effective amount of an oligomeric compound of this invention can be a dose ranging from 0.001 mg/kg to 50.0 mg/kg.

In the methods of this invention, target mRNA expression can be reduced in a subject for at least 5 days. In certain embodiments, target mRNA expression can be reduced in a subject for at least 10 days, or 15 days.

In the methods of this disclosure, the administration of an oligomeric compound may not result in an inflammatory response.

In further embodiments, this invention includes methods for inhibiting expression of a target gene in a cell, by treating the cell with an oligomeric compound of this invention.

In additional embodiments, this invention includes methods for inhibiting expression of a target gene in a mammal, by administering to the mammal a composition containing an oligomeric compound of this invention.

In some embodiments, a UNA oligomer targeted to a transthyretin nucleic acid, TTR, can be used as an active agent for preventing or treating amyloid neuropathy, amyloidosis, or amyloidosis related to transthyretin in a subject in need thereof.

In further embodiments, a UNA oligomer targeted to an apolipoprotein B nucleic acid, APOB, can be used as an active agent for preventing or treating hypercholesterolemia, or cholesterol disorder in a subject in need thereof.

In additional embodiments, a UNA oligomer targeted to a proprotein convertase subtilisin/kexin type 9 nucleic acid, PCSK9, can be used as an active agent for preventing or treating hypercholesterolemia, or cholesterol disorder in a subject in need thereof.

In certain embodiments, a UNA oligomer targeted to an apolipoprotein C-III nucleic acid, APOC3 or APOCIII, can be used as an active agent for preventing or treating hypertriglyceridemia, or lipoprotein disorder in a subject in need thereof.

In some embodiments, a UNA oligomer targeted to a sequence of an HBV genome, HBV (Hepatitis B virus), can be used as an active agent for preventing or treating a disease associated with HBV infection, in a subject in need thereof.

Pharmaceutical Compositions

In some aspects, this invention provides pharmaceutical compositions containing an oligomeric compound and a pharmaceutically acceptable carrier.

A pharmaceutical composition can be capable of local or systemic administration. In some aspects, a pharmaceutical composition can be capable of any modality of administration. In certain aspects, the administration can be intravenous, subcutaneous, pulmonary, intramuscular, intraperitoneal, dermal, oral, or nasal administration.

Embodiments of this invention include pharmaceutical compositions containing an oligomeric compound in a lipid formulation.

In some embodiments, a pharmaceutical composition may comprise one or more lipids selected from cationic lipids, anionic lipids, sterols, pegylated lipids, and any combination of the foregoing.

In certain embodiments, a pharmaceutical composition can be substantially free of liposomes.

In further embodiments, a pharmaceutical composition can include liposomes or nanoparticles.

Some examples of lipids and lipid compositions for delivery of an active molecule of this invention are given in WO/2015/074085, which is hereby incorporated by reference in its entirety.

In additional embodiments, a pharmaceutical composition can contain an oligomeric compound within a viral or bacterial vector.

A pharmaceutical composition of this disclosure may include carriers, diluents or excipients as are known in the art. Examples of pharmaceutical compositions are described, for example, in *Remington's Pharmaceutical Sciences*, Mack Publishing Co. (A. R. Gennaro ed. 1985).

Examples of excipients for a pharmaceutical composition include antioxidants, suspending agents, dispersing agents, preservatives, buffering agents, tonicity agents, and surfactants.

EXAMPLES

Example 1: Luciferase Reporter Assay

Luciferase-based reporter plasmid was constructed based on psiCHECK™2 vector (Promega, Madison, Wis.).

Reporter p(1-20) was generated with oligonucleotides containing the sequence from position 1 through 2500 relative to Eco RI digestion site cloned into the multiple cloning region downstream of the stop codon of the SV40 promoted Renilla luciferase gene in psiCHECK™2, which made the expression of Renilla luciferase gene under the regulation of the artificial 3'UTR sequence. Renilla luciferase activity was then used as an indicator of the effect of the artificial 3'UTR on transcript stability and translation efficiency. The psiCHECK™-2 Vector also contained a constitutively expressed Firefly luciferase gene, which served as an internal control to normalize transfection efficiency.

A total of 5,000 HepB3 cells (American Type Culture Collection) were plated onto a well of 96-well plate one day before the transfection. The cells were incubated at 37° C. in 100 µl of DMEM (Life Technologies, Carlsbad, Calif.) supplemented with 0.1 mM nonessential amino acids and 10% FBS (Life Technologies, Carlsbad, Calif.). The culture medium was changed to 90 µl of fresh medium just before the transfection. The reporter plasmid and UNA Oligomer were co-transfected with transfection reagent, Lipofectamine™ 3000 (Life Technologies, Carlsbad, Calif.) was used to transfect reporter plasmid (100 ng) and a various amount of UNA Oligomer together with P3000 into the cells according to manufacturer's instruction.

Dual-Luciferase Reporter Assay System (DLR assay system, Promega, Madison, Wis.) was used to perform dual-reporter assays on psiCHECK2 based reporter systems. Twenty-four hours after transfection, the cells were washed gently with phosphate buffered saline once. A 50 µl well of Passive Lysis Buffer (Promega, Madison, Wis.) was added to the cells and incubated with gentle rocking for 20 min at room temperature. Luciferase activities were measured using Cytation 3 imaging reader (BioTek, Winooski, Vt.) and the effect of the UNA Oligomer on reporter expression was calculated based on ratio of Renilla/Firefly to normalize cell number and transfection efficiency.

Example 2: UNA Oligomer Stability

Protocol for determining the stability of a UNA oligomer measured against snake venom PDE I or FBS. The UNA oligomer (1-10 uM) is incubated with $2\times10^{-4}$ units/µL Phosphodiesterase I from Crotalus adamanteus venom (code#: VPH, Worthington Biochemial, USA) in 20 mM Tris-HCl (pH 8.0), 100 mM NaCl, 15 mM MgCl2 or 10-50% of FBS (final concentration) at 37° C. After 0.5, 1 and 2 h, aliquots (3 µL) are taken from the mixture and the reaction is stopped by mixing with 5.3 µL of 0.5 M EDTA (pH 8.0). The sample is loaded on a 15% native polyacrylamide gel for electrophoresis. The gel is stained with SYBR SAFE and visualized under UV.

Example 3: UNA Oligomer Longevity

Protocol for determining the longevity of a UNA oligomer in vitro or in vivo. Total RNA samples from cell lines or mouse tissue are isolated. Reverse transcription reactions are performed using SuperScript III First-Strand (Life Technologies) with RNA samples, 50 nM stem-loop RT primer. All Reverse transcriptase reactions are run in triplicate. Real-time PCR is performed using a standard TaqMan PCR kit protocol with 400 nM universal primer, 400 nM gene-specific primer, and 300 nM TaqMan probe on an Applied Biosystems 7900HT Sequence Detection System. One µl of cDNA template is added to a final volume of 25 µl reaction. All reactions are carried out in triplicate with no template control as well as no-RT sample. The reactions are incubated in a 384-well plate at 95° C. for 10 min, followed by 40 cycles of 95° C. for 15 s and 60° C. for 1 min. All reactions are run in triplicate. The threshold cycle (CT) value, which is defined as the fractional cycle number at which the fluorescence passes the fixed threshold, is converted into an absolute copy number using a standard curve from a synthetic UNA oligomer.

Example 4: A Dose dependent inhibitory effect of UNA oligomers targeted to HBV was observed in Hep3B cells transfected with a reporter construct having HBV binding sites UNA oligomers of this invention were found to exhibit IC50 as shown in Table 28. In Table 28, the UNA oligomers correspond to the structures shown in Tables 24-27 having the same reference position.

TABLE 28

| IC50 of UNA oligomers targeted to HBV | | |
|---|---|---|
| No. | Reference Position | IC50 pM Hep3B cells (6 days) |
| 1 | 244 | 917 |
| 2 | 245 | 328 |
| 3 | 246 | 816 |
| 4 | 247 | — |
| 5 | 248 | 148 |
| 6 | 249 | — |
| 7 | 250 | — |
| 8 | 251 | 554 |
| 9 | 252 | 374 |
| 10 | 253 | 703 |
| 11 | 254 | 44 |
| 12 | 256 | 8 |
| 13 | 374 | 1601 |
| 14 | 376 | 16 |
| 15 | 378 | 114 |
| 16 | 380 | 7 |
| 17 | 409 | 328 |
| 18 | 411 | 58 |
| 19 | 412 | 298 |
| 20 | 413 | 123 |
| 21 | 414 | 363 |
| 22 | 1525 | — |
| 23 | 1575 | 65 |
| 24 | 1576 | 137 |
| 25 | 1577 | 472 |
| 26 | 1578 | 63 |
| 27 | 1579 | — |
| 28 | 1580 | 255 |
| 29 | 1581 | 22 |
| 30 | 1776 | 461 |
| 31 | 1777 | 26 |
| 32 | 1779 | 348 |
| 33 | 1780 | 151 |
| 34 | 1781 | 227 |
| 35 | 1782 | 177 |
| 36 | 1818 | 49 |

The experimental results in Table 28 show that the UNA oligomers provide stable, surprisingly long-lasting activity for modulating gene expression. The activities of the UNA oligomers as measured by Luciferase reporter were in the picomolar range, six days after transfection.

Example 5: In addition, in experimental results the UNA oligomers of this invention targeted to HBV provide increased activity in vitro, as well as increased potency in vivo Further, in experimental results the UNA oligomers of this invention targeted to HBV provide increased enzymatic stability.

Moreover, in experimental results the UNA oligomers of this invention targeted to HBV provide long lasting activity in vitro, as well as long lasting potency in vivo.

UNA oligomers of this invention targeted to HBV provide long acting properties, and reduce the dose levels required for efficacious therapy.

Example 6: A dose dependent inhibitory effect of UNA oligomers targeted to TTR was observed in HepG2 cells, as shown in Table 29

TABLE 29

IC50 of UNA oligomers targeted to TTR

| Structure | IC50 pM (TTR) HepG2 cells |
|---|---|
| SEQ ID NOs: 237 and 238 | 5.23 |
| SEQ ID NOs: 239 and 240 | 3.89 |
| SEQ ID NOs: 241 and 242 | 4.98 |
| SEQ ID NOs: 243 and 244 | 7.20 |
| SEQ ID NOs: 245 and 246 | 24.8 |
| SEQ ID NOs: 247 and 248 | 19.3 |

The experimental results in Table 29 show that TTR UNA oligomers provided stable, potent knockdown of TTR gene expression.

Example 7: A dose dependent inhibitory effect of TTR UNA oligomers was observed in HepG2 cells, as shown in Table 30

TABLE 30

IC50 of UNA oligomers targeted to TTR

| Structure | IC50 pM (TTR) HepG2 cells |
|---|---|
| SEQ ID NOs: 261 and 262 | 3.20 |
| SEQ ID NOs: 263 and 264 | 2.23 |
| SEQ ID NOs: 265 and 266 | 3.36 |
| SEQ ID NOs: 267 and 268 | 6.41 |
| SEQ ID NOs: 269 and 270 | 6.67 |
| SEQ ID NOs: 271 and 272 | 6.58 |

The experimental results in Table 30 show that TTR UNA oligomers provided stable, potent knockdown of TTR gene expression.

Example 8: In addition, in experimental results the UNA oligomers of this invention targeted to TTR provide increased activity in vitro, as well as increased potency in vivo Further, in experimental results the UNA oligomers of this invention targeted to TTR provide increased enzymatic stability.

Moreover, in experimental results the UNA oligomers of this invention targeted to TTR provide long lasting activity in vitro, as well as long lasting potency in vivo.

UNA oligomers of this invention targeted to TTR provide long acting properties, and reduce the dose levels required for efficacious therapy.

Example 9: A dose dependent inhibitory effect of UNA oligomers targeted to APOB was observed in mouse Hepa1-6 cells, as shown in Table 31

TABLE 31

IC50 of UNA oligomers targeted to APOB

| Structure | IC50 nM (APOB) Hepa1-6 cells |
|---|---|
| SEQ ID NOs: 285 and 286 | 1.31 |
| SEQ ID NOs: 287 and 288 | 0.48 |
| SEQ ID NOs: 289 and 290 | 34 |
| SEQ ID NOs: 291 and 292 | 0.68 |
| SEQ ID NOs: 293 and 294 | 15 |

The experimental results in Table 31 show that APOB UNA oligomers provided stable, potent knockdown of APOB gene expression.

Example 10: A dose dependent inhibitory effect of UNA oligomers targeted to APOB was observed in mouse Hep3B cells, as shown in Table 32

TABLE 32

IC50 of UNA oligomers targeted to APOB

| Structure | IC50 nM (APOB) Hep3B cells |
|---|---|
| SEQ ID NOs: 285 and 286 | 0.26 |
| SEQ ID NOs: 287 and 288 | 0.80 |
| SEQ ID NOs: 289 and 290 | 0.54 |
| SEQ ID NOs: 291 and 292 | 0.21 |
| SEQ ID NOs: 293 and 294 | 0.88 |

The experimental results in Table 32 show that APOB UNA oligomers provided stable, potent knockdown of APOB gene expression.

Example 11: In addition, in experimental results the UNA oligomers of this invention targeted to APOB provide increased activity in vitro, as well as increased potency in vivo Further, in experimental results the UNA oligomers of this invention targeted to APOB provide increased enzymatic stability.

Moreover, in experimental results the UNA oligomers of this invention targeted to APOB provide long lasting activity in vitro, as well as long lasting potency in vivo.

UNA oligomers of this invention targeted to APOB provide long acting properties, and reduce the dose levels required for efficacious therapy.

Example 12: A dose dependent inhibitory effect of
UNA oligomers targeted to PCSK9 was observed
in mouse Hepa1-6 cells, as shown in Table 33

TABLE 33

| IC50 of UNA oligomers targeted to PCSK9 | |
| --- | --- |
| Structure | IC50 nM (PCSK9) Hepa1-6 cells |
| SEQ ID NOs: 305 and 306 | 2.37 |
| SEQ ID NOs: 307 and 308 | 1.56 |
| SEQ ID NOs: 309 and 310 | 1.78 |

The experimental results in Table 33 show that PCSK9 UNA oligomers provided stable, potent knockdown of PCSK9 gene expression.

Example 13: A dose dependent inhibitory effect of
UNA oligomers targeted to PCSK9 was observed
in mouse Hep3B cells, as shown in Table 34

TABLE 34

| IC50 of UNA oligomers targeted to PCSK9 | |
| --- | --- |
| Structure | IC50 nM (PCSK9) Hep3B cells |
| SEQ ID NOs: 305 and 306 | 2.27 |
| SEQ ID NOs: 307 and 308 | 0.70 |
| SEQ ID NOs: 309 and 310 | 3.94 |

The experimental results in Table 34 show that PCSK9 UNA oligomers provided stable, potent knockdown of PCSK9 gene expression.

Example 14: In addition, in experimental results
the UNA oligomers of this invention targeted to
PCSK9 provide increased activity in vitro, as well
as increased potency in vivo Further, in experimental results the UNA oligomers of this invention targeted to PCSK9 provide increased enzymatic stability.

Moreover, in experimental results the UNA oligomers of this invention targeted to PCSK9 provide long lasting activity in vitro, as well as long lasting potency in vivo.

UNA oligomers of this invention targeted to PCSK9 provide long acting properties, and reduce the dose levels required for efficacious therapy.

Example 15: A dose dependent inhibitory effect of
UNA oligomers targeted to APOC3 was observed
in mouse Hep3B cells, as shown in Table 35

TABLE 35

| IC50 of UNA oligomers targeted to APOC3 | |
| --- | --- |
| Structure | IC50 pM (APOC3) Hep3B cells |
| SEQ ID NOs: 317 and 318 | 2.8 |
| SEQ ID NOs: 319 and 320 | 2.4 |
| SEQ ID NOs: 321 and 322 | 3.4 |
| SEQ ID NOs: 323 and 324 | 17.5 |

The experimental results in Table 35 show that APOC3 UNA oligomers provided stable, potent knockdown of APOC3 gene expression.

Example 16: In addition, in experimental results
the UNA oligomers of this invention targeted to
APOC3 provide increased activity in vitro, as well
as increased potency in vivo Further, in experimental results the UNA oligomers of this invention targeted to APOC3 provide increased enzymatic stability.

Moreover, in experimental results the UNA oligomers of this invention targeted to APOC3 provide long lasting activity in vitro, as well as long lasting potency in vivo.

UNA oligomers of this invention targeted to APOC3 provide long acting properties, and reduce the dose levels required for efficacious therapy.

All publications, patents and literature specifically mentioned herein are incorporated by reference for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be encompassed by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A UNA oligomer comprising a first strand and a second strand, each of the strands being 19-29 monomers in length, the monomers comprising UNA monomers and nucleic acid monomers, wherein the oligomer has a duplex structure of from 14 to 29 monomers in length, wherein the second strand is a guide strand for RNA interference and the first strand is a passenger strand for RNA interference, wherein the first strand has the sequence of SEQ ID NO:263, the second strand has the sequence of SEQ ID NO:264, and the UNA oligomer reduces expression of a target gene.

2. The UNA oligomer of claim 1, wherein the target gene is a viral gene of TTR.

3. The UNA oligomer of claim 1, wherein the UNA oligomer has long lasting activity in vitro.

4. The UNA oligomer of claim 1, wherein the UNA oligomer has long lasting potency in vivo.

5. A pharmaceutical composition comprising the UNA oligomer of claim 1 and a pharmaceutically acceptable carrier, diluent, or adjuvant.

6. A method for reducing expression of a gene comprising contacting a cell with the UNA oligomer of claim 1.

7. A method for treating amyloid neuropathy or amyloidosis in a subject in need thereof comprising administration of the composition of claim 5.

8. The method of claim 6, wherein the gene is TTR.

9. The method of claim 7, wherein the amyloidosis is amyloidosis related to transthyretin.

* * * * *

SEQUENCE LISTING

<160> NUMBER OF SEQ ID NOS: 414

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 1
nnnnnnnnnn nnnnnnnnnn nn                                              22

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 2
nnnnnnnnnn nnnnnnnnnn n                                               21

<210> SEQ ID NO 3
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 3
nnnnnnnnnn nnnnnnnnnn nn                                              22

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 4
nnnnnnnnnn nnnnnnnnnn n                                               21

```
<210> SEQ ID NO 5
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 5
nnnnnnnnnn nnnnnnnnnn nn                                              22

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 6
nnnnnnnnnn nnnnnnnnnn n                                               21

<210> SEQ ID NO 7
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 7
nnnnnnnnnn nnnnnnnnnn nn                                              22

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 8
nnnnnnnnnn nnnnnnnnnn n                                               21

<210> SEQ ID NO 9
<211> LENGTH: 22
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 9
nnnnnnnnnn nnnnnnnnnn nn                                            22

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 10
nnnnnnnnnn nnnnnnnnnn n                                             21

<210> SEQ ID NO 11
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 11
nnnnnnnnnn nnnnnnnnnn nn                                            22

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 12
nnnnnnnnnn nnnnnnnnnn n                                             21

<210> SEQ ID NO 13
<211> LENGTH: 22
<212> TYPE: RNA
<213> ORGANISM: Artificial Sequence
<220> FEATURE:
<223> OTHER INFORMATION: Description of Artificial Sequence: Synthetic
```

```
          oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 13
nnnnnnnnnn nnnnnnnnnn nn                                              22

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 14
nnnnnnnnnn nnnnnnnnnn n                                               21

<210> SEQ ID NO 15
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 15
nnnnnnnnnn nnnnnnnnnn nn                                              22

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 16
nnnnnnnnnn nnnnnnnnnn n                                               21

<210> SEQ ID NO 17
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 17
nnnnnnnnnn nnnnnnnnnn nn                                            22

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 18
nnnnnnnnnn nnnnnnnnnn n                                             21

<210> SEQ ID NO 19
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 19
nnnnnnnnnn nnnnnnnnnn nn                                            22

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 20
nnnnnnnnnn nnnnnnnnnn n                                             21

<210> SEQ ID NO 21
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
``` based on a propane-1,2,3-tri-yl-trisoxy structure

<400> SEQUENCE: 21
nnnnnnnnnn nnnnnnnnnn nn        22

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 22
nnnnnnnnnn nnnnnnnnnn n        21

<210> SEQ ID NO 23
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 23
nnnnnnnnnn nnnnnnnnnn nn        22

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 24
nnnnnnnnnn nnnnnnnnnn n        21

<210> SEQ ID NO 25
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 25
nnnnnnnnnn nnnnnnnnnn nn                                               22

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 26
nnnnnnnnnn nnnnnnnnn n                                                 21

<210> SEQ ID NO 27
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 27
nnnnnnnnnn nnnnnnnnnn nn                                               22

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 28
nnnnnnnnnn nnnnnnnnn n                                                 21

<210> SEQ ID NO 29
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 29
nnnnnnnnnn nnnnnnnnnn nn                                               22

```
<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 30
nnnnnnnnnn nnnnnnnnnn n                                                   21

<210> SEQ ID NO 31
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 31
nnnnnnnnnn nnnnnnnnnn nn                                                  22

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 32
nnnnnnnnnn nnnnnnnnnn n                                                   21

<210> SEQ ID NO 33
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 33
nnnnnnnnnn nnnnnnnnnn nn                                                  22

<210> SEQ ID NO 34
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 34
nnnnnnnnnn nnnnnnnnnn n                                                   21

<210> SEQ ID NO 35
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 35
nnnnnnnnnn nnnnnnnnnn nn                                                  22

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 36
nnnnnnnnnn nnnnnnnnnn n                                                   21

<210> SEQ ID NO 37
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 37
nnnnnnnnnn nnnnnnnnnn nn                                                  22

<210> SEQ ID NO 38
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 38
nnnnnnnnnn nnnnnnnnnn n                                            21

<210> SEQ ID NO 39
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 39
nnnnnnnnnn nnnnnnnnnn nn                                           22

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 40
nnnnnnnnnn nnnnnnnnnn n                                            21

<210> SEQ ID NO 41
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 41
nnnnnnnnnn nnnnnnnnnn nn                                           22

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 42
nnnnnnnnnn nnnnnnnnnn n                                                 21

<210> SEQ ID NO 43
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 43
nnnnnnnnnn nnnnnnnnnn nn                                                22

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 44
nnnnnnnnnn nnnnnnnnnn n                                                 21

<210> SEQ ID NO 45
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 45
nnnnnnnnnn nnnnnnnnnn nn                                                22

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified
based on a propane-1,2,3-tri-yl-trisoxy structure

<400> SEQUENCE: 46
nnnnnnnnnn nnnnnnnnnn n                                              21

<210> SEQ ID NO 47
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 47
nnnnnnnnnn nnnnnnnnnn nn                                             22

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 48
nnnnnnnnnn nnnnnnnnnn n                                              21

<210> SEQ ID NO 49
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 49
nnnnnnnnnn nnnnnnnnnn nn                                             22

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

```
<400> SEQUENCE: 50
nnnnnnnnnn nnnnnnnnnn n                                              21

<210> SEQ ID NO 51
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 51
nnnnnnnnnn nnnnnnnnnn nn                                             22

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 52
nnnnnnnnnn nnnnnnnnnn n                                              21

<210> SEQ ID NO 53
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 53
nnnnnnnnnn nnnnnnnnnn nn                                             22

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 54
nnnnnnnnnn nnnnnnnnnn n                                              21
```

-continued

```
<210> SEQ ID NO 55
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 55
nnnnnnnnnn nnnnnnnnnn nn                                             22

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 56
nnnnnnnnnn nnnnnnnnnn n                                              21

<210> SEQ ID NO 57
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 57
nnnnnnnnnn nnnnnnnnnn nn                                             22

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 58
nnnnnnnnnn nnnnnnnnnn n                                              21

<210> SEQ ID NO 59
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 59
nnnnnnnnnn nnnnnnnnnn n                                              21

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 60
nnnnnnnnnn nnnnnnnnnn n                                              21

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 61
nnnnnnnnnn nnnnnnnnnn n                                              21

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 62
nnnnnnnnnn nnnnnnnnnn n                                              21

<210> SEQ ID NO 63
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 63
nnnnnnnnnn nnnnnnnnnn n                                            21

<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 64
nnnnnnnnnn nnnnnnnnnn n                                            21

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 65
nnnnnnnnnn nnnnnnnnnn n                                            21

<210> SEQ ID NO 66
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 66
nnnnnnnnnn nnnnnnnnnn n                                            21

<210> SEQ ID NO 67
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 67
nnnnnnnnnn nnnnnnnnn n                                                21

<210> SEQ ID NO 68
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 68
nnnnnnnnnn nnnnnnnnn n                                                21

<210> SEQ ID NO 69
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 69
nnnnnnnnnn nnnnnnnnn n                                                21

<210> SEQ ID NO 70
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 70
nnnnnnnnnn nnnnnnnnn n                                                21

<210> SEQ ID NO 71
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
```

<223> OTHER INFORMATION: Any natural, non-natural, modified, or
      chemically-modified nucleotide; may or may not be modified
      based on a propane-1,2,3-tri-yl-trisoxy structure

<400> SEQUENCE: 71
nnnnnnnnnn nnnnnnnnnn n                                            21

<210> SEQ ID NO 72
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 72
nnnnnnnnnn nnnnnnnnnn n                                            21

<210> SEQ ID NO 73
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 73
nnnnnnnnnn nnnnnnnnnn n                                            21

<210> SEQ ID NO 74
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 74
nnnnnnnnnn nnnnnnnnnn n                                            21

<210> SEQ ID NO 75
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 75
nnnnnnnnnn nnnnnnnnn n                                                  21

<210> SEQ ID NO 76
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 76
nnnnnnnnnn nnnnnnnnn n                                                  21

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 77
nnnnnnnnnn nnnnnnnnn n                                                  21

<210> SEQ ID NO 78
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 78
nnnnnnnnnn nnnnnnnnn n                                                  21

<210> SEQ ID NO 79
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 79
nnnnnnnnnn nnnnnnnnnn n                                         21

<210> SEQ ID NO 80
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 80
nnnnnnnnnn nnnnnnnnnn n                                         21

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 81
nnnnnnnnnn nnnnnnnnnn n                                         21

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 82
nnnnnnnnnn nnnnnnnnnn n                                         21

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 83
nnnnnnnnnn nnnnnnnnnn n                                         21

-continued

```
<210> SEQ ID NO 84
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 84
nnnnnnnnnn nnnnnnnnn n                                              21

<210> SEQ ID NO 85
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 85
nnnnnnnnnn nnnnnnnnn n                                              21

<210> SEQ ID NO 86
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 86
nnnnnnnnnn nnnnnnnnn n                                              21

<210> SEQ ID NO 87
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 87
nnnnnnnnnn nnnnnnnnn n                                              21

<210> SEQ ID NO 88
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 88
nnnnnnnnnn nnnnnnnnnn n                                                    21

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 89
nnnnnnnnnn nnnnnnnnnn n                                                    21

<210> SEQ ID NO 90
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 90
nnnnnnnnnn nnnnnnnnnn n                                                    21

<210> SEQ ID NO 91
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 91
nnnnnnnnnn nnnnnnnnnn n                                                    21

<210> SEQ ID NO 92
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 92
nnnnnnnnnn nnnnnnnnnn n                                              21

<210> SEQ ID NO 93
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 93
nnnnnnnnnn nnnnnnnnnn n                                              21

<210> SEQ ID NO 94
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 94
nnnnnnnnnn nnnnnnnnnn n                                              21

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 95
nnnnnnnnnn nnnnnnnnnn n                                              21

<210> SEQ ID NO 96
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 96
nnnnnnnnnn nnnnnnnnn n                                              21

<210> SEQ ID NO 97
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 97
nnnnnnnnnn nnnnnnnnn n                                              21

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 98
nnnnnnnnnn nnnnnnnnn n                                              21

<210> SEQ ID NO 99
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 99
nnnnnnnnnn nnnnnnnnn n                                              21

<210> SEQ ID NO 100
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
``` based on a propane-1,2,3-tri-yl-trisoxy structure

<400> SEQUENCE: 100
nnnnnnnnnn nnnnnnnnn n                                                      21

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 101
nnnnnnnnnn nnnnnnnnn n                                                      21

<210> SEQ ID NO 102
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 102
nnnnnnnnnn nnnnnnnnn n                                                      21

<210> SEQ ID NO 103
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 103
nnnnnnnnnn nnnnnnnnn n                                                      21

<210> SEQ ID NO 104
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 104
nnnnnnnnnn nnnnnnnnn n                                      21

<210> SEQ ID NO 105
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 105
nnnnnnnnnn nnnnnnnnn n                                      21

<210> SEQ ID NO 106
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 106
nnnnnnnnnn nnnnnnnnn n                                      21

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 107
nnnnnnnnnn nnnnnnnnn n                                      21

<210> SEQ ID NO 108
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 108
nnnnnnnnnn nnnnnnnnn n                                      21

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 109
nnnnnnnnnn nnnnnnnnnn n                                              21

<210> SEQ ID NO 110
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 110
nnnnnnnnnn nnnnnnnnnn n                                              21

<210> SEQ ID NO 111
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 111
nnnnnnnnnn nnnnnnnnnn n                                              21

<210> SEQ ID NO 112
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 112
nnnnnnnnnn nnnnnnnnnn n                                              21

<210> SEQ ID NO 113
<211> LENGTH: 21

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 113
nnnnnnnnnn nnnnnnnnnn n                                                21

<210> SEQ ID NO 114
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 114
nnnnnnnnnn nnnnnnnnnn n                                                21

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 115
nnnnnnnnnn nnnnnnnnnn n                                                21

<210> SEQ ID NO 116
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 116
nnnnnnnnnn nnnnnnnnnn n                                                21

<210> SEQ ID NO 117
<211> LENGTH: 21
<212> TYPE: RNA
<213> ORGANISM: Artificial Sequence
<220> FEATURE:
```

-continued

```
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 117
nnnnnnnnnn nnnnnnnnnn n                                              21

<210> SEQ ID NO 118
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 118
nnnnnnnnnn nnnnnnnnnn n                                              21

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 119
nnnnnnnnnn nnnnnnnnnn n                                              21

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 120
nnnnnnnnnn nnnnnnnnnn n                                              21

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 121
nnnnnnnnnn nnnnnnnnnn n                                              21

<210> SEQ ID NO 122
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 122
nnnnnnnnnn nnnnnnnnnn n                                              21

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 123
nnnnnnnnnn nnnnnnnnnn n                                              21

<210> SEQ ID NO 124
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 124
nnnnnnnnnn nnnnnnnnnn n                                              21

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
``` chemically-modified nucleotide; may or may not be modified
      based on a propane-1,2,3-tri-yl-trisoxy structure

<400> SEQUENCE: 125
nnnnnnnnnn nnnnnnnnnn n                                            21

<210> SEQ ID NO 126
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 126
nnnnnnnnnn nnnnnnnnnn n                                            21

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 127
nnnnnnnnnn nnnnnnnnnn n                                            21

<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 128
nnnnnnnnnn nnnnnnnnnn n                                            21

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

```
<400> SEQUENCE: 129
nnnnnnnnnn nnnnnnnnn n                                          21

<210> SEQ ID NO 130
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 130
nnnnnnnnnn nnnnnnnnn n                                          21

<210> SEQ ID NO 131
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 131
nnnnnnnnnn nnnnnnnnn n                                          21

<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 132
nnnnnnnnnn nnnnnnnnn n                                          21

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 133
nnnnnnnnnn nnnnnnnnn n                                          21
```

-continued

```
<210> SEQ ID NO 134
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 134
nnnnnnnnnn nnnnnnnnnn n                                            21

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 135
nnnnnnnnnn nnnnnnnnnn n                                            21

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 136
nnnnnnnnnn nnnnnnnnnn n                                            21

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 137
nnnnnnnnnn nnnnnnnnnn n                                            21

<210> SEQ ID NO 138
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 138
nnnnnnnnnn nnnnnnnnnn n                                              21

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 139
nnnnnnnnnn nnnnnnnnnn n                                              21

<210> SEQ ID NO 140
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 140
nnnnnnnnnn nnnnnnnnnn n                                              21

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 141
nnnnnnnnnn nnnnnnnnnn n                                              21

<210> SEQ ID NO 142
<211> LENGTH: 21
<212> TYPE: RNA
<213> ORGANISM: Artificial Sequence
```

<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 142
nnnnnnnnnn nnnnnnnnnn n                                              21

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 143
nnnnnnnnnn nnnnnnnnnn n                                              21

<210> SEQ ID NO 144
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 144
nnnnnnnnnn nnnnnnnnnn n                                              21

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 145
nnnnnnnnnn nnnnnnnnnn n                                              21

<210> SEQ ID NO 146
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 146
nnnnnnnnnn nnnnnnnnnn n                                             21

<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 147
nnnnnnnnnn nnnnnnnnnn n                                             21

<210> SEQ ID NO 148
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 148
nnnnnnnnnn nnnnnnnnnn n                                             21

<210> SEQ ID NO 149
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 149
nnnnnnnnnn nnnnnnnnnn n                                             21

<210> SEQ ID NO 150
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
```

<223> OTHER INFORMATION: Any natural, non-natural, modified, or
      chemically-modified nucleotide; may or may not be modified
      based on a propane-1,2,3-tri-yl-trisoxy structure

<400> SEQUENCE: 150
nnnnnnnnnn nnnnnnnnnn n                                              21

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 151
nnnnnnnnnn nnnnnnnnnn n                                              21

<210> SEQ ID NO 152
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 152
nnnnnnnnnn nnnnnnnnnn n                                              21

<210> SEQ ID NO 153
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 153
nnnnnnnnnn nnnnnnnnnn n                                              21

<210> SEQ ID NO 154
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 154
nnnnnnnnnn nnnnnnnnn n                                               21

<210> SEQ ID NO 155
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 155
nnnnnnnnnn nnnnnnnnn n                                               21

<210> SEQ ID NO 156
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 156
nnnnnnnnnn nnnnnnnnn n                                               21

<210> SEQ ID NO 157
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 157
nnnnnnnnnn nnnnnnnnn n                                               21

<210> SEQ ID NO 158
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 158
nnnnnnnnnn nnnnnnnnn n                                      21

<210> SEQ ID NO 159
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 159 nnnnnnnnn nnnnnnnnn n                                       21

<210> SEQ ID NO 160
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 160 nnnnnnnnn nnnnnnnnn n                                       21

<210> SEQ ID NO 161
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 161 nnnnnnnnn nnnnnnnnn n                                       21

<210> SEQ ID NO 162
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 162 nnnnnnnnn nnnnnnnnn n                                       21

<210> SEQ ID NO 163
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 163
nnnnnnnnnn nnnnnnnnn n                                              21

<210> SEQ ID NO 164
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 164
nnnnnnnnnn nnnnnnnnn n                                              21

<210> SEQ ID NO 165
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 165
nnnnnnnnnn nnnnnnnnn n                                              21

<210> SEQ ID NO 166
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 166
nnnnnnnnnn nnnnnnnnn n                                              21

<210> SEQ ID NO 167
<211> LENGTH: 21
<212> TYPE: RNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 167
nnnnnnnnnn nnnnnnnnnn n                                            21

<210> SEQ ID NO 168
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 168
nnnnnnnnnn nnnnnnnnnn n                                            21

<210> SEQ ID NO 169
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 169
nnnnnnnnnn nnnnnnnnnn n                                            21

<210> SEQ ID NO 170
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 170
nnnnnnnnnn nnnnnnnnnn n                                            21

<210> SEQ ID NO 171
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 171
nnnnnnnnnn nnnnnnnnnn n                                                  21

<210> SEQ ID NO 172
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 172
nnnnnnnnnn nnnnnnnnnn n                                                  21

<210> SEQ ID NO 173
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 173
nnnnnnnnnn nnnnnnnnnn n                                                  21

<210> SEQ ID NO 174
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 174
nnnnnnnnnn nnnnnnnnnn n                                                  21

<210> SEQ ID NO 175
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 175
nnnnnnnnnn nnnnnnnnnn n                                              21

<210> SEQ ID NO 176
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 176
nnnnnnnnnn nnnnnnnnnn n                                              21

<210> SEQ ID NO 177
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 177
nnnnnnnnnn nnnnnnnnnn n                                              21

<210> SEQ ID NO 178
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 178
nnnnnnnnnn nnnnnnnnnn n                                              21

<210> SEQ ID NO 179
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
``` based on a propane-1,2,3-tri-yl-trisoxy structure

<400> SEQUENCE: 179
nnnnnnnnnn nnnnnnnnn n                                              21

<210> SEQ ID NO 180
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 180
nnnnnnnnnn nnnnnnnnn n                                              21

<210> SEQ ID NO 181
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 181
nnnnnnnnnn nnnnnnnnn n                                              21

<210> SEQ ID NO 182
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 182
nnnnnnnnnn nnnnnnnnn n                                              21

<210> SEQ ID NO 183
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 183
nnnnnnnnnn nnnnnnnnn n                                           21

<210> SEQ ID NO 184
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 184
nnnnnnnnnn nnnnnnnnn n                                           21

<210> SEQ ID NO 185
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 185
nnnnnnnnnn nnnnnnnnn n                                           21

<210> SEQ ID NO 186
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 186
nnnnnnnnnn nnnnnnnnn n                                           21

<210> SEQ ID NO 187
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 187
nnnnnnnnnn nnnnnnnnn n                                           21

```
<210> SEQ ID NO 188
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 188
nnnnnnnnnn nnnnnnnnnn n                                            21

<210> SEQ ID NO 189
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 189
nnnnnnnnnn nnnnnnnnnn n                                            21

<210> SEQ ID NO 190
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 190
nnnnnnnnnn nnnnnnnnnn n                                            21

<210> SEQ ID NO 191
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 191
nnnnnnnnnn nnnnnnnnnn n                                            21

<210> SEQ ID NO 192
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 192
nnnnnnnnnn nnnnnnnnnn n                                            21

<210> SEQ ID NO 193
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 193
nnnnnnnnnn nnnnnnnnnn n                                            21

<210> SEQ ID NO 194
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 194
nnnnnnnnnn nnnnnnnnnn n                                            21

<210> SEQ ID NO 195
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 195
nnnnnnnnnn nnnnnnnnnn n                                            21

<210> SEQ ID NO 196
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 196
nnnnnnnnnn nnnnnnnnnn n                                               21

<210> SEQ ID NO 197
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 197
nnnnnnnnnn nnnnnnnnnn n                                               21

<210> SEQ ID NO 198
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 198
nnnnnnnnnn nnnnnnnnnn n                                               21

<210> SEQ ID NO 199
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 199
nnnnnnnnnn nnnnnnnnnn n                                               21

<210> SEQ ID NO 200
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 200
nnnnnnnnnn nnnnnnnnnn n                                          21

<210> SEQ ID NO 201
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 201
nnnnnnnnnn nnnnnnnnnn n                                          21

<210> SEQ ID NO 202
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 202
nnnnnnnnnn nnnnnnnnnn n                                          21

<210> SEQ ID NO 203
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 203
nnnnnnnnnn nnnnnnnnnn n                                          21

<210> SEQ ID NO 204
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified
based on a propane-1,2,3-tri-yl-trisoxy structure

<400> SEQUENCE: 204
nnnnnnnnnn nnnnnnnnnn n                                        21

<210> SEQ ID NO 205
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 205
nnnnnnnnnn nnnnnnnnnn n                                        21

<210> SEQ ID NO 206
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 206
nnnnnnnnnn nnnnnnnnnn n                                        21

<210> SEQ ID NO 207
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 207
nnnnnnnnnn nnnnnnnnnn n                                        21

<210> SEQ ID NO 208
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

```
<400> SEQUENCE: 208
nnnnnnnnnn nnnnnnnnn n                                                21

<210> SEQ ID NO 209
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 209
nnnnnnnnnn nnnnnnnnn n                                                21

<210> SEQ ID NO 210
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 210
nnnnnnnnnn nnnnnnnnn n                                                21

<210> SEQ ID NO 211
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 211
nnnnnnnnnn nnnnnnnnn n                                                21

<210> SEQ ID NO 212
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 212
nnnnnnnnnn nnnnnnnnn n                                                21
```

```
<210> SEQ ID NO 213
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 213
nnnnnnnnnn nnnnnnnnnn n                                                  21

<210> SEQ ID NO 214
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 214
nnnnnnnnnn nnnnnnnnnn n                                                  21

<210> SEQ ID NO 215
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 215
nnnnnnnnnn nnnnnnnnnn n                                                  21

<210> SEQ ID NO 216
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 216
nnnnnnnnnn nnnnnnnnnn n                                                  21

<210> SEQ ID NO 217
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 217
nnnnnnnnnn nnnnnnnnnn n                                                    21

<210> SEQ ID NO 218
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 218
nnnnnnnnnn nnnnnnnnnn n                                                    21

<210> SEQ ID NO 219
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 219
nnnnnnnnnn nnnnnnnnnn n                                                    21

<210> SEQ ID NO 220
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 220
nnnnnnnnnn nnnnnnnnnn n                                                    21

<210> SEQ ID NO 221
<211> LENGTH: 21
<212> TYPE: RNA
<213> ORGANISM: Artificial Sequence
```

-continued

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 221
nnnnnnnnnn nnnnnnnnnn n                                           21

<210> SEQ ID NO 222
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 222
nnnnnnnnnn nnnnnnnnnn n                                           21

<210> SEQ ID NO 223
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 223
nnnnnnnnnn nnnnnnnnnn n                                           21

<210> SEQ ID NO 224
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 224
nnnnnnnnnn nnnnnnnnnn n                                           21

<210> SEQ ID NO 225
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 225
nnnnnnnnnn nnnnnnnnnn n                                              21

<210> SEQ ID NO 226
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 226
nnnnnnnnnn nnnnnnnnnn n                                              21

<210> SEQ ID NO 227
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 227
nnnnnnnnnn nnnnnnnnnn n                                              21

<210> SEQ ID NO 228
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 228
nnnnnnnnnn nnnnnnnnnn n                                              21

<210> SEQ ID NO 229
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
```

```
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 229
nnnnnnnnnn nnnnnnnnnn n                                              21

<210> SEQ ID NO 230
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 230
nnnnnnnnnn nnnnnnnnnn n                                              21

<210> SEQ ID NO 231
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 231
nnnnnnnnnn nnnnnnnnnn n                                              21

<210> SEQ ID NO 232
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 232
nnnnnnnnnn nnnnnnnnnn n                                              21

<210> SEQ ID NO 233
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure
```

```
<400> SEQUENCE: 233
nnnnnnnnnn nnnnnnnnnn n                                              21

<210> SEQ ID NO 234
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 234
nnnnnnnnnn nnnnnnnnnn n                                              21

<210> SEQ ID NO 235
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 235
nnnnnnnnnn nnnnnnnnnn n                                              21

<210> SEQ ID NO 236
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 236
nnnnnnnnnn nnnnnnnnnn n                                              21

<210> SEQ ID NO 237
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
uguaaccaag aguauuccau u                                              21

<210> SEQ ID NO 238
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 238
uggaauacuc uugguuacau u                                              21

<210> SEQ ID NO 239
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
uguaaccaag aguauuccau u                                              21

<210> SEQ ID NO 240
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
uggaauacuc uugguuacau u                                              21

<210> SEQ ID NO 241
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
uguaaccaag aguauuccau u                                              21

<210> SEQ ID NO 242
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
uggaauacuc uugguuacau u                                              21

<210> SEQ ID NO 243
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
uguaaccaag aguauuccau u                                              21

<210> SEQ ID NO 244
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 244
uggaauacuc uugguuacau u                                                   21

<210> SEQ ID NO 245
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
uguaaccaag aguauuccau u                                                   21

<210> SEQ ID NO 246
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
uggaauacuc uugguuacau u                                                   21

<210> SEQ ID NO 247
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
gguaaccaag aguauuccau u                                                   21

<210> SEQ ID NO 248
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
uggaauacuc uugguuacuu u                                                   21

<210> SEQ ID NO 249
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
uguaaccaag aguauuccau u                                                   21

<210> SEQ ID NO 250
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 250
uggaauacuc uugguuacau u                                              21

<210> SEQ ID NO 251
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
uguaaccaag aguauuccau u                                              21

<210> SEQ ID NO 252
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
uggaauacuc uugguuacau u                                              21

<210> SEQ ID NO 253
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
uguaaccaag aguauuccau u                                              21

<210> SEQ ID NO 254
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
uggaauacuc uugguuacau u                                              21

<210> SEQ ID NO 255
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
uguaaccaag aguauuccau u                                              21

<210> SEQ ID NO 256
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 256
uggaauacuc uugguuacau u                                              21

<210> SEQ ID NO 257
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
uguaaccaag aguauuccau u                                              21

<210> SEQ ID NO 258
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
uggaauacuc uugguuacau u                                              21

<210> SEQ ID NO 259
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
gguaaccaag aguauuccau u                                              21

<210> SEQ ID NO 260
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
uggaauacuc uugguuacuu u                                              21

<210> SEQ ID NO 261
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
gaaccaagag uauuccauuu u                                              21

<210> SEQ ID NO 262
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
aauggaauac ucuugguucu u                                              21

<210> SEQ ID NO 263
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
gaaccaagag uauuccauuu u                                              21

<210> SEQ ID NO 264
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
aauggaauac ucuugguucu u                                              21

<210> SEQ ID NO 265
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
gaaccaagag uauuccauuu u                                              21

<210> SEQ ID NO 266
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
aauggaauac ucuugguucu u                                              21

<210> SEQ ID NO 267
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
gaaccaagag uauuccauuu u                                              21

<210> SEQ ID NO 268
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 268
aauggaauac ucuugguucu u                                              21

<210> SEQ ID NO 269
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
gaaccaagag uauuccauuu u                                              21

<210> SEQ ID NO 270
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
aauggaauac ucuugguucu u                                              21

<210> SEQ ID NO 271
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
caaccaagag uauuccauuu u                                              21

<210> SEQ ID NO 272
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
aauggaauac ucuugguugu u                                              21

<210> SEQ ID NO 273
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
gaaccaagag uauuccauuu u                                              21

<210> SEQ ID NO 274
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
```
aauggaauac ucuugguucu u                                              21

<210> SEQ ID NO 275
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
gaaccaagag uauuccauuu u                                              21

<210> SEQ ID NO 276
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
aauggaauac ucuugguucu u                                              21

<210> SEQ ID NO 277
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
gaaccaagag uauuccauuu u                                              21

<210> SEQ ID NO 278
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
aauggaauac ucuugguucu u                                              21

<210> SEQ ID NO 279
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
gaaccaagag uauuccauuu u                                              21

<210> SEQ ID NO 280
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
aauggaauac ucuugguucu u                                              21

<210> SEQ ID NO 281
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
gaaccaagag uauuccauuu u                                              21

<210> SEQ ID NO 282
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
aauggaauac ucuugguucu u                                              21

<210> SEQ ID NO 283
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
caaccaagag uauuccauuu u                                              21

<210> SEQ ID NO 284
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
aauggaauac ucuugguugu u                                              21

<210> SEQ ID NO 285
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
ggaaucuuau auuugaucca a                                              21

<210> SEQ ID NO 286
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
uuggaucaaa uauaagauuc c                                              21

<210> SEQ ID NO 287
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
ggaaucuuau auuugaucca auu                                           23

<210> SEQ ID NO 288
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
uuggaucaaa uauaagauuc cuu                                           23

<210> SEQ ID NO 289
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
ggaaucuuau auuugaucca auu                                           23

<210> SEQ ID NO 290
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
uuggaucaaa uauaagauuc cuu                                           23

<210> SEQ ID NO 291
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
ggaaucuuau auuugaucca auu                                           23

<210> SEQ ID NO 292
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
uuggaucaaa uauaagauuc cuu                                           23

<210> SEQ ID NO 293
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
ggaaucuuau auuugaucca auu                                           23

<210> SEQ ID NO 294
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
uuggaucaaa uauaagauuc cuu                                           23

<210> SEQ ID NO 295
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
ggaaucuuau auuugaucca a                                             21

<210> SEQ ID NO 296
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
uuggaucaaa uauaagauuc c                                             21

<210> SEQ ID NO 297
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
ggaaucuuau auuugaucca auu                                           23

<210> SEQ ID NO 298
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
uuggaucaaa uauaagauuc cuu                                           23

```
<210> SEQ ID NO 299
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
ggaaucuuau auuugaucca auu                                          23

<210> SEQ ID NO 300
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
uuggaucaaa uauaagauuc cuu                                          23

<210> SEQ ID NO 301
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
ggaaucuuau auuugaucca auu                                          23

<210> SEQ ID NO 302
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
uuggaucaaa uauaagauuc cuu                                          23

<210> SEQ ID NO 303
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
ggaaucuuau auuugaucca auu                                          23

<210> SEQ ID NO 304
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
uuggaucaaa uauaagauuc cuu                                          23

<210> SEQ ID NO 305
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
gccuggaguu uauucggaau u                                              21

<210> SEQ ID NO 306
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
uuccgaauaa acuccaggcu u                                              21

<210> SEQ ID NO 307
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
gccuggaguu uauucggaau u                                              21

<210> SEQ ID NO 308
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
uuccgaauaa acuccaggcu u                                              21

<210> SEQ ID NO 309
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
ggccuggagu uuauucggaa uu                                             22

<210> SEQ ID NO 310
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
uuccgaauaa acuccaggcu u                                              21

<210> SEQ ID NO 311
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
gccuggaguu uauucggaau u                                              21

<210> SEQ ID NO 312
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
uuccgaauaa acuccaggcu u                                              21

<210> SEQ ID NO 313
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
gccuggaguu uauucggaau u                                              21

<210> SEQ ID NO 314
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
uuccgaauaa acuccaggcu u                                              21

<210> SEQ ID NO 315
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
ggccuggagu uuauucggaa uu                                             22

<210> SEQ ID NO 316
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
uuccgaauaa acuccaggcu u                                              21

<210> SEQ ID NO 317
<211> LENGTH: 21
<212> TYPE: RNA
```

<213> ORGANISM: Artificial Sequence
<220> FEATURE:
<223> OTHER INFORMATION: Description of Artificial Sequence: Synthetic oligonucleotide

<400> SEQUENCE: 317
aaaagggaca guauucucau u               21

<210> SEQ ID NO 318
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 318
ugagaauacu gucccuuuuu u               21

<210> SEQ ID NO 319
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 319
aaaagggaca guauucucau u               21

<210> SEQ ID NO 320
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 320
ugagaauacu gucccuuuuu u               21

<210> SEQ ID NO 321
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 321
aaaagggaca guauucucau u               21

<210> SEQ ID NO 322
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 322
ugagaauacu gucccuuuuu u               21

<210> SEQ ID NO 323
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 323
aaaagggaca guauucucau u                                              21

<210> SEQ ID NO 324
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
ugagaauacu gucccuuuuu u                                              21

<210> SEQ ID NO 325
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
aaaagggaca guauucucau u                                              21

<210> SEQ ID NO 326
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
ugagaauacu gucccuuuuu u                                              21

<210> SEQ ID NO 327
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
aaaagggaca guauucucau u                                              21

<210> SEQ ID NO 328
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
ugagaauacu gucccuuuuu u                                              21

<210> SEQ ID NO 329
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 329
aaaagggaca guauucucau u                                              21

<210> SEQ ID NO 330
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
ugagaauacu gucccuuuuu u                                              21

<210> SEQ ID NO 331
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
aaaagggaca guauucucau u                                              21

<210> SEQ ID NO 332
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
ugagaauacu gucccuuuuu u                                              21

<210> SEQ ID NO 333
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
cgcaccucuc uuuacgcggu u                                              21

<210> SEQ ID NO 334
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
gacucguggu ggacuucucu u                                              21

<210> SEQ ID NO 335
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 335
ucguggugga cuucucucau u                                              21

<210> SEQ ID NO 336
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
uggauguguc ugcggcguuu u                                              21

<210> SEQ ID NO 337
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
ccgugugcac uucgcuucau u                                              21

<210> SEQ ID NO 338
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338
gugugcacuu cgcuucaccu u                                              21

<210> SEQ ID NO 339
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339
ugugcacuuc gcuucaccuu u                                              21

<210> SEQ ID NO 340
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
gugcacuucg cuucaccucu u                                              21

<210> SEQ ID NO 341
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
gcacuucgcu ucaccucugu u                                           21

<210> SEQ ID NO 342
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
ucuagacucg ugguggacuu u                                           21

<210> SEQ ID NO 343
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
cuagacucgu gguggacuuu u                                           21

<210> SEQ ID NO 344
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
uagacucgug guggacuucu u                                           21

<210> SEQ ID NO 345
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
agacucgugg uggacuucuu u                                           21

<210> SEQ ID NO 346
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
ggaggcugua ggcauaaauu u                                           21

<210> SEQ ID NO 347
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 347
gaggcuguag gcauaaauuu u                                              21

<210> SEQ ID NO 348
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
ggcuguaggc auaaauuggu u                                              21

<210> SEQ ID NO 349
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
gcuguaggca uaaauugguu u                                              21

<210> SEQ ID NO 350
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
cuguaggcau aaauuggucu u                                              21

<210> SEQ ID NO 351
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
uguaggcaua aauuggucuu u                                              21

<210> SEQ ID NO 352
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
gugguggacu ucucucaauu u                                              21

<210> SEQ ID NO 353
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
```
ccgcguaaag agaggugcgu u                                           21

<210> SEQ ID NO 354
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
gagaagucca ccacgagucu u                                           21

<210> SEQ ID NO 355
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
ugagagaagu ccaccacgau u                                           21

<210> SEQ ID NO 356
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
aacgccgcag acacauccau u                                           21

<210> SEQ ID NO 357
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
ugaagcgaag ugcacacggu u                                           21

<210> SEQ ID NO 358
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
ggugaagcga agugcacacu u                                           21

<210> SEQ ID NO 359
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
aggugaagcg aagugcacau u                                             21

<210> SEQ ID NO 360
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
gaggugaagc gaagugcacu u                                             21

<210> SEQ ID NO 361
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
cagaggugaa gcgaagugcu u                                             21

<210> SEQ ID NO 362
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
aguccaccac gagucuagau u                                             21

<210> SEQ ID NO 363
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
aaguccacca cgagucuagu u                                             21

<210> SEQ ID NO 364
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
gaaguccacc acgagucuau u                                             21

<210> SEQ ID NO 365
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
agaaguccac cacgagucuu u                                             21

<210> SEQ ID NO 366
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
auuuaugccu acagccuccu u                                              21

<210> SEQ ID NO 367
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
aauuuaugcc uacagccucu u                                              21

<210> SEQ ID NO 368
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
ccaauuuaug ccuacagccu u                                              21

<210> SEQ ID NO 369
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
accaauuuau gccuacagcu u                                              21

<210> SEQ ID NO 370
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
gaccaauuua ugccuacagu u                                              21

<210> SEQ ID NO 371
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
agaccaauuu augccuacau u                                              21

<210> SEQ ID NO 372
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
auugagagaa guccaccacu u                                              21

<210> SEQ ID NO 373
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
uucaagccuc caagcugugu u                                              21

<210> SEQ ID NO 374
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
ucaagccucc aagcugugcu u                                              21

<210> SEQ ID NO 375
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
caagccucca agcugugccu u                                              21

<210> SEQ ID NO 376
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
aagccuccaa gcugugccuu u                                              21

<210> SEQ ID NO 377
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
gaugugucug cggcguuuuu u                                              21

```
<210> SEQ ID NO 378
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
ugugucugcg gcguuuuauu u                                              21

<210> SEQ ID NO 379
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
ugucugcggc guuuuaucau u                                              21

<210> SEQ ID NO 380
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
aacuuuuuca ccucugccuu u                                              21

<210> SEQ ID NO 381
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
gagucuagac ucgugguggu u                                              21

<210> SEQ ID NO 382
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
agucuagacu cgugguggau u                                              21

<210> SEQ ID NO 383
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
gucuagacuc gugguggacu u                                              21

<210> SEQ ID NO 384
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
cauccugcug cuaugccucu u                                              21

<210> SEQ ID NO 385
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
uccugcugcu augccucauu u                                              21

<210> SEQ ID NO 386
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
ccugcugcua ugccucaucu u                                              21

<210> SEQ ID NO 387
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
cugcugcuau gccucaucuu u                                              21

<210> SEQ ID NO 388
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
ugcugcuaug ccucaucuuu u                                              21

<210> SEQ ID NO 389
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
acucguggug gacuucucuu u                                              21

<210> SEQ ID NO 390
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
cucguggugg acuucucucu u                                              21

<210> SEQ ID NO 391
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
cgugugcacu ucgcuucacu u                                              21

<210> SEQ ID NO 392
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
ugcacuucgc uucaccucuu u                                              21

<210> SEQ ID NO 393
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
cacuucgcuu caccucugcu u                                              21

<210> SEQ ID NO 394
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
cacagcuugg aggcuugaau u                                              21

<210> SEQ ID NO 395
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
gcacagcuug gaggcuugau u                                              21

<210> SEQ ID NO 396
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 396
ggcacagcuu ggaggcuugu u                                            21

<210> SEQ ID NO 397
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
aggcacagcu uggaggcuuu u                                            21

<210> SEQ ID NO 398
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
aaaacgccgc agacacaucu u                                            21

<210> SEQ ID NO 399
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
auaaaacgcc gcagacacau u                                            21

<210> SEQ ID NO 400
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
ugauaaaacg ccgcagacau u                                            21

<210> SEQ ID NO 401
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
aggcagaggu gaaaaaguuu u                                            21

<210> SEQ ID NO 402
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 402
ccaccacgag ucuagacucu u                                            21

<210> SEQ ID NO 403
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
uccaccacga gucuagacuu u                                            21

<210> SEQ ID NO 404
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
guccaccacg agucuagacu u                                            21

<210> SEQ ID NO 405
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
gaggcauagc agcaggaugu u                                            21

<210> SEQ ID NO 406
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
augaggcaua gcagcaggau u                                            21

<210> SEQ ID NO 407
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
gaugaggcau agcagcaggu u                                            21

<210> SEQ ID NO 408
<211> LENGTH: 21
<212> TYPE: RNA
<213> ORGANISM: Artificial Sequence
<220> FEATURE:
```

<223> OTHER INFORMATION: Description of Artificial Sequence: Synthetic
oligonucleotide

<400> SEQUENCE: 408
agaugaggca uagcagcagu u                                              21

<210> SEQ ID NO 409
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 409
aagaugaggc auagcagcau u                                              21

<210> SEQ ID NO 410
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 410
agagaagucc accacgaguu u                                              21

<210> SEQ ID NO 411
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 411
gagagaaguc caccacgagu u                                              21

<210> SEQ ID NO 412
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 412
gugaagcgaa gugcacacgu u                                              21

<210> SEQ ID NO 413
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 413
agaggugaag cgaagugcau u                                              21

<210> SEQ ID NO 414
<211> LENGTH: 21
<212> TYPE: RNA
<213> ORGANISM: Artificial Sequence
<220> FEATURE:
<223> OTHER INFORMATION: Description of Artificial Sequence: Synthetic

```
        oligonucleotide

<400> SEQUENCE: 414
gcagagguga agcgaagugu u                                              21
```